US005489683A

United States Patent [19]

Borzatta et al.

[11] Patent Number: 5,489,683

[45] Date of Patent: Feb. 6, 1996

[54] PIPERIDINE-TRIAZINE COMPOUNDS SUITABLE FOR USE AS STABILISERS FOR ORGANIC MATERIALS

[75] Inventors: Valerio Borzatta; Graziano Vignali; Fabrizio Guizzardi, all of Bologna, Italy

[73] Assignee: Ciba-Geigy Corporation, Tarrytown, N.Y.

[21] Appl. No.: 219,049

[22] Filed: Mar. 28, 1994

[30] Foreign Application Priority Data

Apr. 5, 1993 [IT] Italy ................................ MI93A0661

[51] Int. Cl.$^6$ ...................... C07D 251/40; C07D 251/48; C07D 251/14

[52] U.S. Cl. .......................... 544/209; 544/113; 544/194; 544/198; 544/219; 540/553

[58] Field of Search .................................... 544/194, 198, 544/209, 219, 113; 540/553

[56] References Cited

U.S. PATENT DOCUMENTS

| | | | |
|---|---|---|---|
| 3,925,376 | 12/1975 | Chalmers et al. | 260/248 |
| 4,108,829 | 8/1978 | Cassandrini et al. | 260/45.8 |
| 4,288,593 | 9/1981 | Rody | 544/198 |
| 4,376,836 | 3/1983 | Wiezer et al. | 524/100 |
| 4,433,145 | 2/1984 | Wiezer et al. | 544/198 |
| 4,476,302 | 10/1984 | Wiezer et al. | 544/198 |
| 4,496,726 | 1/1985 | Wiezer et al. | 544/198 |
| 5,102,928 | 4/1992 | Borzatta | 524/100 |

FOREIGN PATENT DOCUMENTS

| | | |
|---|---|---|
| 0029522 | 6/1981 | European Pat. Off. . |
| 0117229 | 8/1984 | European Pat. Off. . |
| 0299925 | 1/1989 | European Pat. Off. . |
| 0314472 | 5/1989 | European Pat. Off. . |
| 0319480 | 6/1989 | European Pat. Off. . |
| 0345220 | 12/1989 | European Pat. Off. . |
| 0350444 | 1/1990 | European Pat. Off. . |
| 0354185 | 2/1990 | European Pat. Off. . |
| 0399953 | 11/1990 | European Pat. Off. . |
| 0410934 | 1/1991 | European Pat. Off. . |
| 904401 | 6/1986 | France . |
| 0904840 | 9/1986 | France . |

OTHER PUBLICATIONS

D. Hodgeman, Applied Science Publishers Ltd (1982) Dev. in Polymer Degredation–4 pp. 190–191.

Norman Grassie & Gerald Scott: Polymer degredation & Stabilization, Cambridge Univ. Press (1985) pp. 161–164.

Derwent 84–214929/35, 1983.

Derwent 86–265175/41, 1985.

Derwent 86–189962/30, 1985.

*Primary Examiner*—Yogendra N. Gupta

*Attorney, Agent, or Firm*—Luther A. Hall; Michele A. Kovaleski

[57] ABSTRACT

Novel piperidine-triazine compounds of the formula (Ia) and (Ib) suitable for use as light stabilizers, heat stabilizers and oxidation stabilizers for organic materials. The meanings of $R_1$, $R_2$, $R_3$, $G_1$, $G_2$, $L_1$, $L_2$, m and n are defined in the text.

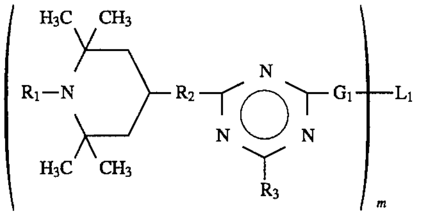

(Ia)

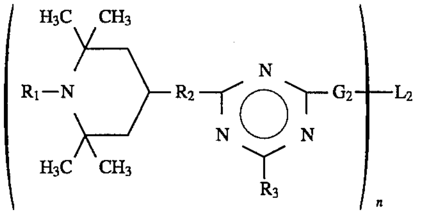

(Ib)

6 Claims, No Drawings

PIPERIDINE-TRIAZINE COMPOUNDS SUITABLE FOR USE AS STABILISERS FOR ORGANIC MATERIALS

The present invention relates to novel piperidine-triazine compounds, to their use as light stabilisers, heat stabilisers and oxidation stabilisers for organic materials, particularly synthetic polymers, and to the organic materials thus stabilised.

The stabilisation of synthetic polymers with derivatives of 2,2,6,6-tetramethylpiperidine containing one or more 1,3,5-triazine tings has been described in numerous patents, in particular in U.S. Pat. Nos. 3,925,376, 4,108,829, 4,288,593, 4,376,836, 4,476,302, 4,496,726, in European Patents 117 229, 299 925, 314 472 and 410 934 and in BE Patents 904 401 and 904 840.

The present invention relates to novel compounds of formula (Ia) or (Ib)

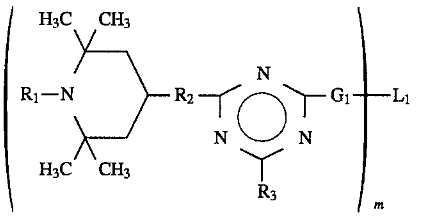

(Ia)

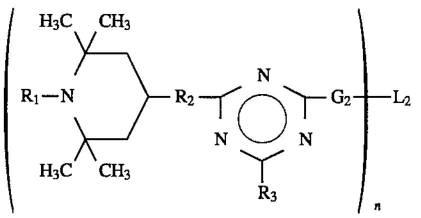

(Ib)

in which $R_1$ is hydrogen, $C_1$–$C_8$alkyl, O., OH, $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or substituted on the phenyl with 1, 2 or 3 $C_1$–$C_4$alkyls, or aliphatic $C_1$–$C_8$acyl;

$R_2$ is

—O— or 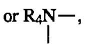

where $R_4$ is hydrogen, $C_1$–$C_{18}$alkyl, $C_5$–$C_{12}$cycloalkyl, which is unsubstituted or substituted with 1, 2 or 3 $C_1$–$C_4$alkyls, $C_7$–$C_9$phenylalkyl which is unsubstituted or substituted on the phenyl with 1, 2 or 3 $C_1$–$C_4$alkyls, tetrahydrofurfuryl, a group of formula (II)

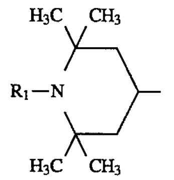

(II)

or $C_2$–$C_4$alkyl which is substituted in the 2, 3 or 4 position with $C_1$–$C_8$alkoxy, with di($C_1$–$C_4$alkyl)amino or with a group of formula (III)

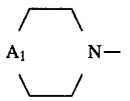

(III)

where $A_1$ is a direct bond, —O—, —$CH_2$—, —$CH_2CH_2$— or

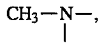

or $R_2$ is also one of the groups of formulae (IVa)–(IVc)

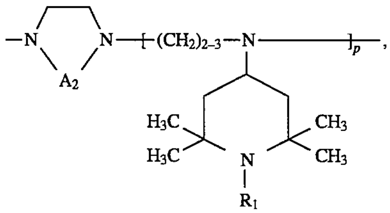

(IVa)

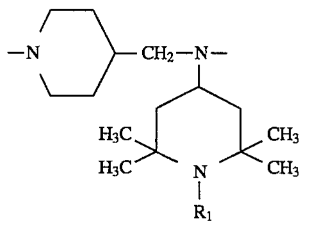

(IVb)

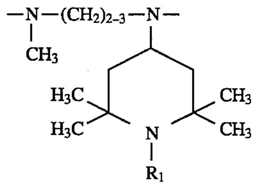

(IVc)

in which $R_1$ is as defined above, $A_2$ is —$CH_2CH_2$—, —CO—, —COCO—, —$CH_2$CO— or —$COCH_2$CO— and p is zero or 1, the nitrogen atom substituted with the piperidyl group being bound to the triazine ring of formula (Ia) or (Ib);

$R_3$ is a group of formula (V)

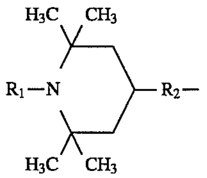

(V)

with $R_1$ and R2 as defined above, or a group of formula (III) or an $R_5$O— or

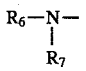

group, where $R_5$, $R_6$ and $R_7$, which are identical or different, are hydrogen, $C_1$–$C_{18}$alkyl, $C_5$–$C_{12}$cycloalkyl which is unsubstituted or substituted with 1, 2 or 3 $C_1$–$C_4$alkyls, $C_3$–$C_{18}$alkenyl, phenyl which is unsubstituted or substituted with 1, 2 or 3 $C_1$–$C_4$alkyls or $C_1$–$C_4$alkoxy, $C_7$–$C_9$phenylalkyl which is unsubstituted or substituted on the phenyl with 1, 2 or 3 $C_1$–$C_4$alkyls, tetrahydrofurfuryl or $C_2$–$C_4$alkyl which is substituted in the 2, 3 or 4 position with $C_1$–$C_8$alkoxy or with di($C_1$–$C_4$alkyl)amino or with a group of formula (III);

$G_1$ is a group of formula (VI)

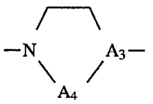 (VI)

in which $A_3$ is a $>N-(R_8-A_5)_q$ or

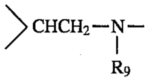

group, where $R_8$ is $C_2$–$C_6$alkylene, $A_5$ is —O— or

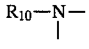

and q is zero or 1, $R_9$ and $R_{10}$ having any one of the meanings given for $R_4$, and $A_4$ is $-CH_2CH_2-$ or, if $A_3$ is $>N-$, $A_4$ is also a

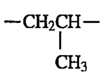 or 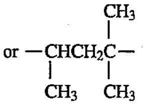

group, the endocyclic nitrogen atom of the formula (VI) being able to be bound to the triazine ting or to the $L_1$ group of formula (Ia);

$G_2$ is a group of formula (VII)

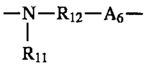 (VII)

in which $R_{11}$ has any one of the meanings given for $R_4$, $R_{12}$ is $C_2$–$C_{12}$alkylene, $C_4$–$C_{12}$alkylene interrupted by 1, 2 or 3 oxygen atoms, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene) or phenylenedi($C_1$–$C_4$alkylene) and $A_6$ is as defined above for $A_5$, the nitrogen atom attached to the $R_{11}$ group being able to be bound to the triazine ring or to the $L_2$ group of formula (Ib);

m is 1, 2, 3 or 4;

if m is 1, $L_1$ is hydrogen, $C_1$–$C_{18}$alkyl, $C_3$–$C_6$alkenyl, $C_7$–$C_9$phenylalkyl which is unsubstituted or substituted on the phenyl with 1, 2 or 3 $C_1$–$C_4$alkyls, aliphatic, cycloaliphatic or aromatic acyl containing not more than 22 carbon atoms or ($C_1$–$C_{18}$alkoxy)carbonyl;

if m is 2, $L_1$ is $C_2$–$C_{12}$alkylene, $C_4$–$C_{12}$alkylene interrupted by 1, 2 or 3 oxygen atoms, phenylenedi($C_1$–$C_4$alkylene), aliphatic, cycloaliphatic or aromatic diacyl containing not more than 20 carbon atoms or one of the groups of formulae (VIIIa)–(VIIId)

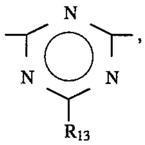 (VIIIa)

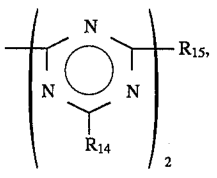 (VIIIb)

-continued

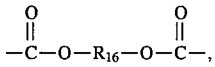 (VIIIc)

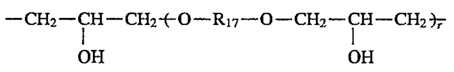 (VIIId)

in which $R_{13}$ has any one of the meanings given for $R_3$ or is a group of formula (IX)

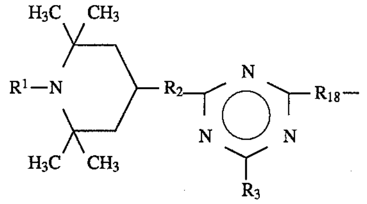 (IX)

where $R_1$, $R_2$ and $R_3$ are as defined above and $R_{18}$ is a group of formula (VI) or a group of formula (VII) as defined above, or $R_{13}$ is also an $R_{18}H$ group, $R_{14}$ has any one of the meanings given for $R_3$ or is a group of formula (IX), $R_{15}$ is a group of formula (Xa) or (Xb)

$-A_7-R_{19}-A_8-$, (Xa)

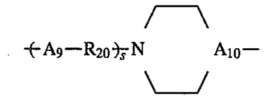 (Xb)

in which $A_7$, $A_8$ and $A_9$, which are identical or different, have any one of the meanings given for $A_5$, $R_{19}$ has any one of the meanings given for $R_{12}$ or is $C_4$–$C_{12}$alkylene interrupted by an

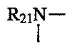

group, where $R_{21}$ has any one of the meanings given for $R_4$ or is an aliphatic, cycloaliphatic or aromatic acyl containing not more than 12 carbon atoms or ($C_1$–$C_{12}$alkoxy)carbonyl, $C_2$–$C_4$alkylidenedi($C_5$–$C_7$cycloalkylene), phenylene or $C_2$–$C_4$alkylidenediphenylene, each phenylene group being unsubstituted or substituted with 1 or 2 $C_1$–$C_4$alkyls, or $R_{19}$ is a

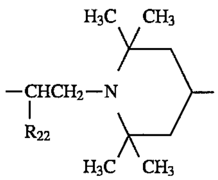

group, with $R_{22}$ being hydrogen or $C_1$–$C_4$alkyl, or a

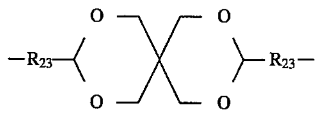

group, $R_{20}$ and $R_{23}$ are $C_2$–$C_6$alkylene, s is zero or 1, $A_{10}$ has any one of the meanings given for $A_3$, $R_{16}$ and $R_{17}$ have any one of the meanings given for $R_{12}$ or are $C_2$–$C_4$alkylidenedi($C_5$–$C_7$cycloalkylene), phenylene or $C_2$–$C_4$alkylidenediphenylene, each phenylene group being unsubstituted or substituted with 1 or 2 $C_1$–$C_4$alkyls, and r is zero or 1;

if m is 3, $L_1$ is aliphatic, cycloaliphatic or aromatic triacyl containing not more than 12 carbon atoms or a group of formula (XIa) or (XIb)

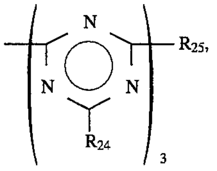

(XIa)

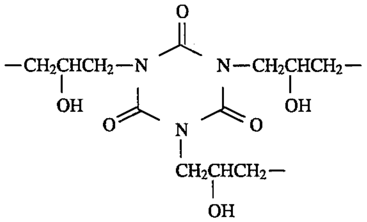

(XIb)

in which $R_{24}$ is as defined above for $R_{14}$ and $R_{25}$ is one of the groups of formulae (XIIa)–(XIId)

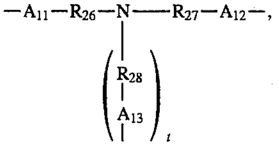

(XIIa)

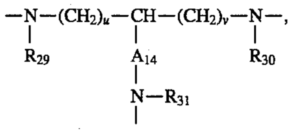

(XIIb)

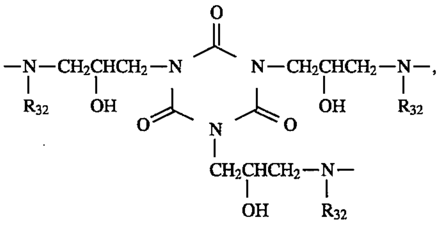

(XIIc)

$R_{33}(O-)_3$ (XIId)

in which $A_{11}$, $A_{12}$ and $A_{13}$, which are identical or different, have any one of the meanings given for $A_5$, $R_{26}$, $R_{27}$ and $R_{28}$, which are identical or different, are $C_2$–$C_6$alkylene, t is zero or 1, $R_{29}$, $R_{30}$, $R_{31}$ and $R_{32}$, which are identical or different, have any one of the meanings given for $R_4$, $A_{14}$ is a direct bond or —$CH_2$—, u and v, which are identical or different, are integers from 2 to 6 and $R_{33}$ is $C_3$–$C_{12}$alkanetriyl;

if m is 4, $L_1$ is aliphatic or aromatic tetraacyl containing not more than 12 carbon atoms, tetrahydrofuran-2,3,4,5-tetracarbonyl or a group of formula (XIII)

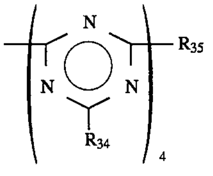

(XIII)

in which $R_{34}$ is as defined above for $R_{14}$ and $R_{35}$ is one of the groups of formulae (XIVa)–(XIVc)

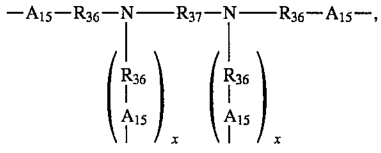

(XIVa)

$R_{38}(O-)_4$ (XIVb)

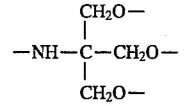

(XIVc)

in which $A_{15}$ has any one of the meanings given for $A_5$, $R_{36}$ and $R_{37}$, which are identical or different, are $C_2$–$C_6$alkylene, x is zero or 1 and $R_{38}$ is $C_4$–$C_{12}$alkanetetrayl;

n is 2, 3 or 4;

if n is 2, $L_2$ is one of the groups of formulae (VIIIb)–(VIIId) as defined above;

if n is 3, $L_2$ is a group of formula (XIa) or (XIb) as defined above;

if n is 4, $L_2$ is tetrahydrofuran-2,3,4,5-tetracarbonyl or a group of formula (XIII) as defined above.

Examples of alkyl containing not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$–$C_4$alkyl substituted with $C_1$–$C_8$alkoxy, preferably with $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted with di($C_1$–$C_4$alkyl)amino, preferably with dimethylamino or with diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Preferred examples of $C_2$–$C_4$alkyl substituted with a group of formula (III) are the

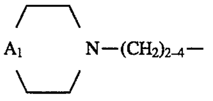

groups, the

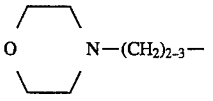

group being particularly preferred.

Examples of alkoxy containing not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy.

Preferred examples of $R_1$ are $C_6$–$C_{12}$alkoxy, in particular heptoxy and octoxy.

Examples of $C_5$–$C_{12}$cycloaikyl which is unsubstituted or substituted with 1, 2 or 3 $C_1$–$C_4$alkyls are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted cyclohexyl is preferred.

For $R_1$, examples of $C_5$–$C_{12}$cycloalkoxy are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl containing not more than 18 carbon atoms are allyl, 2-methylallyl, butenyl, hexenyl, undecenyl and octadecenyl. Alkenyls in which the carbon atom in the 1-position is saturated are preferred; allyl is particularly preferred.

Representative examples of phenyl substituted with 1, 2 or 3 $C_1$–$C_4$alkyls or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_9$phenylalkyl which is unsubstituted or substituted on the phenyl with 1, 2 or 3 $C_1$–$C_4$alkyls are benzyl, methylbenzyl, dimethylbenzyl, trimethylbenzyl, t-butylbenzyl and 2-phenylethyl. Benzyl is preferred.

Representative examples of aliphatic, cycloaliphatic or aromatic acyl containing not more than 22 carbon atoms are acetyl, propionyl, butyryl, isobutyryl, pentanoyl, hexanoyl, heptanoyl, octanoyl, 2-ethylhexanoyl, decanoyl, undecanoyl, dodecanoyl, tetradecanoyl, hexadecanoyl, octadecanoyl, eicosanoyl, docosanoyl, cyclohexanecarbonyl, benzoyl, t-butylbenzoyl, 3,5-di-t-butyl-4-hydroxybenzoyl, 3(3,5-di-t-butyl-4-hydroxyphenyl)propionyl, acryloyl, crotonyl and 10-undecenoyl.

Examples of alkylene containing not more than 12 carbon atoms are ethylene, propylene, trimethylene, 2-methyltrimethylene, 2,2-dimethyltrimethylene, tetramethylene, pentamethylene, hexamethylene, trimethylhexamethylene, octamethylene, decamethylene and dodecamethylene.

Examples of $C_4$–$C_{12}$alkylene interrupted by 1, 2 or 3 oxygen atoms are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

If $R_{19}$ is $C_4$–$C_{12}$alkylene interrupted by an

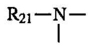

group, representative examples are the

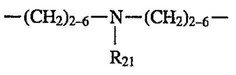

groups, with $R_{21}$ as defined above.

Representative examples of the groups containing 1 or 2 $C_5$–$C_7$cycloalkylene groups are cyclohexylene, methylcyclohexylene, cyclohexylenedimethylene, methylenedicyclohexylene, isopropylidenedicyclohexylene or the

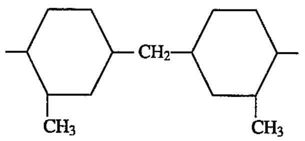

Representative examples of the groups containing 1 or 2 phenylene groups are phenylene, methylphenylene, dimethylphenylene, di-t-butylphenylene, phenylenedimethylene and isopropylidenediphenylene.

Representative examples of aliphatic, cycloaliphatic or aromatic diacyl, containing not more than 20 carbon atoms, are the diacyls derived from oxalic, malonic, ethylmalonic, butylmalonic, dodecylmalonic, octadecylmalonic, succinic, glutaric, adipic, pimelic, suberic, azelaic, sebacic, cyclohexanedicarboxylic, phthalic, isophthalic and terephthalic acids.

Preferred examples of $C_3$–$C_{12}$alkanetriyl are 1,2,3-propanetriyl, 1,2,4-butanetriyl, 1,2,6-hexanetriyl or the

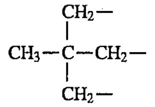

and

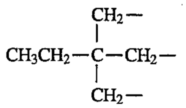

groups.

Representative examples of aliphatic, cycloaliphatic or aromatic triacyl containing not more than 12 carbon atoms are the triacyls derived from methanetricarboxylic, 1,1,2-ethanetricarboxylic, 1,2,3-propanetricarboxylic, citric, 1,2,3-butanetricarboxylic, 1,3,5-cyclohexanetricarboxylic, 1,2,4-benzenetricarboxylic or 1,3,5-benzenetricarboxylic acids.

For $R_{38}$, preferred examples of $C_4$–$C_6$alkanetetrayl are 1,2,3,4-butanetetrayl and the

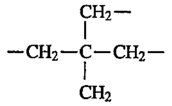

group.

Representative examples of aliphatic or aromatic tetraacyl containing not more than 12 carbon atoms are the tetraacyls derived from 1,1,3,3-propanetetracarboxylic, 1,2,3,4-butanetetracarboxylic or 1,2,4,5-benzenetetracarboxylic acids.

Preferred meanings of $R_1$ are hydrogen, $C_1$–$C_4$alkyl, OH, $C_6$–$C_{12}$alkoxy, $C_5$–$C_8$cycloalkoxy, allyl, benzyl or acetyl, in particular hydrogen or methyl.

Preferred compounds of formula (Ia) or (IIb) are those in which $R_2$ is —O— or

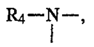

where $R_4$ is hydrogen, $C_1$–$C_{16}$alkyl, $C_5$–$C_8$cycloalkyl which is unsubstituted or substituted with 1, 2 or 3 $C_1$–$C_4$alkyls, benzyl which is unsubstituted or substituted on the phenyl with 1, 2 or 3 $C_1$–$C_4$alkyls, tetrahydrofurfuryl, a group of formula (II), $C_2$–$C_3$alkyl which is substituted in the 2 or 3 position with $C_1$–$C_4$alkoxy, with di($C_1$–$C_4$alkyl)amino or with a group of formula (III), where $A_1$ is a direct bond, —O—, —$CH_2$— or —$CH_2CH_2$— or $R_2$ is also one of the groups of formulae (IVa)-(IVc), in which $A_2$ is —$CH_2CH_2$—, —CO—, —COCO— or —$COCH_2CO$— and p is zero or 1;

$R_3$ is a group of formula (V) or a group of formula (III) or an $R_5$—O— or

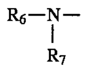

group, where $R_5$, $R_6$ and $R_7$, which are identical or different, are hydrogen, $C_1$–$C_{12}$alkyl, $C_5$–$C_8$cycloalkyl which is unsubstituted or substituted with 1, 2 or 3 $C_1$–$C_4$alkyls, $C_3$–$C_{12}$alkenyl, phenyl which is unsubstituted or substituted with 1, 2 or 3 $C_1$–$C_4$alkyls, or $C_1$–$C_4$alkoxy, benzyl which is unsubstituted or substituted on the phenyl with 1, 2 or 3 $C_1$–$C_4$alkyls, tetrahydrofurfuryl or $C_2$–$C_3$alkyl substituted in the 2 or 3 position with $C_1$–$C_4$alkoxy, with di($C_1$–$C_4$alkyl)amino or with a group of formula (III);

$G_1$ is a group of formula (VI), in which $A_3$ is a >N—($R_8$—$A_5$)$_q$— or

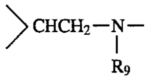

group, where $R_8$ is $C_2$–$C_4$alkylene, $A_5$ is —O— or

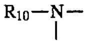

and q is zero or 1, $R_9$ and $R_{10}$ have any one of the meanings given for $R_4$ and $A_4$ is —$CH_2CH_2$— or, if $A_3$ is >N—, $A_4$ is also a

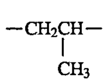 or 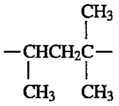

group;

$G_2$ is a group of formula (VII), in which $R_{11}$ has any one of the meanings given for $R_4$, $R_{12}$ is $C_2$–$C_{10}$alkylene, $C_4$–$C_{10}$alkylene interrupted by 1, 2 or 3 oxygen atoms, cyclohexylene, cyclohexylenedimethylene, methylenedicyclohexylene or phenylenedimethylene, $A_6$ is as defined above for $A_5$ and m is 1, 2, 3 or 4;

if m is 1, $L_1$ is hydrogen, $C_1$–$C_{16}$alkyl, $C_3$–$C_4$alkenyl, benzyl which is unsubstituted or substituted on the phenyl with 1, 2 or 3 $C_1$–$C_4$alkyls, aliphatic, cycloaliphatic or aromatic acyl containing not more than 18 carbon atoms or ($C_1$–$C_{18}$alkoxy)carbonyl;

if m is 2, $L_1$ is $C_2$–$C_{10}$alkylene, $C_4$–$C_{10}$alkylene interrupted by 1, 2 or 3 oxygen atoms, phenylenedimethylene, aliphatic, cycloaliphatic or aromatic diacyl containing not more than 18 carbon atoms or one of the groups of formulae (VIIIa)–(VIIId), in which $R_{13}$ has any one of the meanings given for $R_3$ or is a group of formula (IX), where $R_{18}$ is a group of formula (VI) or (VII), of $R_{13}$ is also a —$R_{18}$H group, $R_{14}$ has any one of the meanings given for $R_3$ or is a group of formula (IX), $R_{15}$ is a group of formula (Xa) or (Xb), in which $A_7$, $A_8$ and $A_9$, which are identical or different, have any one of the meanings given for $A_5$, $R_{19}$ has any one of the meanings given for $R_{12}$ or is $C_4$–$C_{10}$alkylene interrupted by an

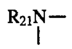

group, where $R_{21}$ has any one of the meanings given for $R_4$ or is aliphatic, cycloaliphatic or aromatic acyl containing not more than 8 carbon atoms or ($C_1$–$C_8$alkoxycarbonyl), isopropylidenedicyclohexylene, phenylene, isopropylidenediphenylene, a

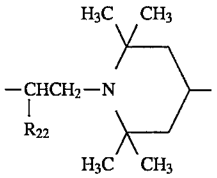

group, with $R_{22}$ being hydrogen or methyl, or a

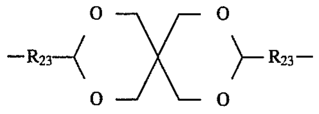

group, $R_{20}$ and $R_{23}$ are $C_2$–$C_4$alkylene, s is zero or 1, $A_{10}$ has any one of the meanings given for $A_3$, $R_{16}$ and $R_{17}$ have any one of the meanings given for $R_{12}$ or are isopropylidenedicyclohexylene, phenylene or isopropylidenediphenylene, and r is zero or 1;

if m is 3, $L_1$ is aliphatic, cycloaliphatic or aromatic triacyl containing not more than 10 carbon atoms or a group of formula (XIa) or (XIb), in which $R_{24}$ is as defined above for $R_{14}$ and $R_{25}$ is one of the groups of formulae (XIIa)–(XIId), in which $A_{11}$, $A_{12}$ and $A_{13}$, which are identical or different, have any one of the meanings given for $A_5$, $R_{26}$, $R_{27}$ and $R_{28}$ which are identical or different, are $C_2$–$C_6$alkylene, t is zero or 1, $R_{29}$, $R_{30}$, $R_{31}$ and $R_{32}$, which are identical or different, have any one of the meanings given for $R_4$, $A_{14}$ is a direct bond or —$CH_2$—, u and v, which are identical or different, are integers from 3 to 6 and $R_{33}$ is $C_3$–$C_{10}$alkanetriyl;

if m is 4, $L_1$ is aliphatic or aromatic tetraacyl containing not more than 10 carbon atoms, tetrahydrofuran-2,3,4,5-tetracarbonyl or a group of formula (XIII), in which $R_{34}$ is as defined above for $R_{14}$ and $R_{35}$ is one of the groups of formulae (XIVa)–(XIVc), in which $A_{15}$ has any one of the meanings given for $A_5$, $R_{36}$ and $R_{37}$, which are identical or different, are $C_2$–$C_4$alkylene, x is zero or 1 and $R_{38}$ is $C_4$–$C_8$alkanetetrayl;

n is 2, 3 or 4 and, if n is 2, $L_2$ is one of the groups of formulae (VIIIb)-(VIIId) as defined above;

if n is 3, $L_2$ is a group of formula (XIa) or (XIb) as defined above;

if n is 4, $L_2$ is tetrahydrofuran-2,3,4,5-tetracarbonyl or a group of formula (XIII) as defined above.

Particularly preferred compounds of formula (Ia) or (Ib) are those in which $R_2$ is —O— or

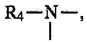, where $R_4$ is hydrogen, $C_1$–$C_{12}$alkyl, cyclohexyl which is unsubstituted or substituted with 1, 2 or 3 $C_1$–$C_4$alkyls, benzyl, tetrahydrofurfuryl, a group of formula (II), $C_2$–$C_3$alkyl which is substituted in the 2 or 3 position with $C_1$–$C_4$alkoxy, with dimethylamino, with diethylamino or with 4-morpholinyl, or $R_2$ is also one of the groups of formula (IVa)–(IVc), in which $A_2$ is —$CH_2CH_2$—, —CO— or —COCO— and p is zero or 1;

$R_3$ is a group of formula (V) or a 4-morpholinyl group or an $R_5$O— or

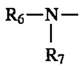

group, where $R_5$, $R_6$ and $R_7$, which are identical or different, are hydrogen, $C_1$–$C_8$alkyl, cyclohexyl which is unsubstituted or substituted with 1, 2 or 3 $C_1$–$C_4$alkyls, $C_3$–$C_{11}$alkenyl, phenyl, benzyl, tetrahydrofurfuryl or $C_2$–$C_3$alkyl which is substituted in the 2 or 3 position with $C_1$–$C_4$alkoxy, with dimethylamino, with diethylamino or with 4-morpholinyl;

$G_1$ is a group of formula (VI), in which $A_3$ is a >N—($R_8$—$A_5$)$_q$— or

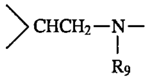

group where $R_8$ is $C_2$–$C_4$alkylene, $A_5$ is —O— or

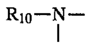

and q is zero or 1, $R_9$ and $R_{10}$ have any one of the meanings given for $R_4$ and $A_4$ is —$CH_2CH_2$— or, if $A_3$ is >N—, $A_4$ is also a

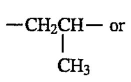 or 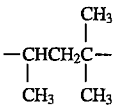

group;

$G_2$ is a group of formula (VII), in which $R_{11}$ has any one of the meanings given for $R_4$, $R_{12}$ is $C_2$–$C_8$alkylene, $C_4$–$C_{10}$alkylene interrupted by 1, 2 or 3 oxygen atoms, cyclohexylenedimethylene, methylenedicyclohexylene or phenylenedimethylene, $A_6$ is as defined above for $A_5$ and m is 1, 2, 3 or 4;

if m is 1, $L_1$ is hydrogen, $C_1$–$C_{12}$alkyl, allyl, 2-methylallyl, benzyl, aliphatic $C_1$–$C_{12}$acyl or ($C_1$–$C_{12}$alkoxy)carbonyl;

if m is 2, $L_1$ is $C_2$–$C_8$alkylene, $C_4$–$C_8$alkylene interrupted by 1, 2 or 3 oxygen atoms, phenylenedimethylene, aliphatic $C_2$–$C_{16}$diacyl or one of the groups of formulae (VIIIa)–(VIIId), in which $R_{13}$ has any one of the meanings given for $R_3$ or is a group of formula (IX), where $R_{18}$ is a group of formula (VI) or (VII), or $R_{13}$ is also a —$R_{18}$H group, $R_{14}$ has any one of the meanings given for $R_3$ or is a group of formula (IX), $R_{15}$ is a group of formula (Xa) or (Xb), in which $A_7$, $A_8$ and $A_9$, which are identical or different, have any one of the meanings given for $A_5$, $R_{19}$ has any one of the meanings given for $R_{12}$ or is $C_4$–$C_{10}$alkylene interrupted by a

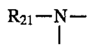

group, where $R_{21}$ has any one of the meanings given for $R_4$ or is aliphatic $C_1$–$C_4$acyl or ($C_1$–$C_4$alkoxy)carbonyl, isopropylidenedicyclohexylene, isopropylidenediphenylene, a

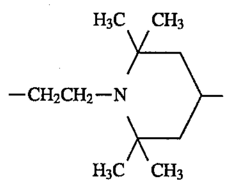

group or a

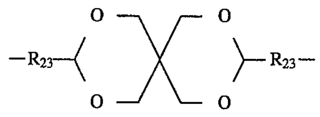

group, $R_{20}$ and $R_{23}$ are $C_2$–$C_4$alkylene, s is zero or 1, $A_{10}$ has any one of the meanings given for $A_3$, $R_{16}$ and $R_{17}$ have any one of the meanings given for $R_{12}$ or are isopropylidenedicyclohexylene or isopropylidenediphenylene and r is zero or 1;

if m is 3, $L_1$ is aliphatic $C_4$–$C_8$triacyl or a group of formula (XIa) or (XIb), in which $R_{24}$ is as defined above for $R_{14}$ and $R_{25}$ is one of the groups of formulae (XIIa)–(XIId), in which $A_{11}$, $A_{12}$ and $A_{13}$, which are identical or different, have any one of the meanings given for $A_5$, $R_{26}$, $R_{27}$ and $R_{28}$, which are identical or different, are $C_2$–$C_4$alkylene, t is zero or 1, $R_{29}$, $R_{30}$, $R_{31}$ and $R_{32}$, which are identical or different, have any one of the meanings given for $R_4$, $A_{14}$ is a direct bond or —$CH_2$—, u and v, which are identical or different, are integers from 3 to 5 and $R_{33}$ is $C_3$–$C_6$alkanetriyl;

if m is 4, $L_1$ is aliphatic $C_6$–$C_8$tetraacyl or a group of formula (XIII), in which $R_{34}$ is as defined above for $R_{14}$ and $R_{35}$ is one of the groups of formulae (XIVa)–(XIVc), in which $A_{15}$ has any one of the meanings given for $A_5$, $R_{36}$ and $R_{37}$, which are identical or different, are $C_2$–$C_4$alkylene, x is zero or 1 and $R_{38}$ is $C_4$–$C_6$alkanetetrayl;

n is 2, 3 or 4 and, if n is 2, $L_2$ is one of the groups of formulae (VIIIb)–(VIIId) as defined above;

if n is 3, $L_2$ is a group of formula (XIa) or (XIb) as defined above and, if n is 4, $L_2$ is a group of formula (XIII) as defined above.

Compounds of formula (Ia) or (Ib) of special interest are those in which $R_2$ is —O— or

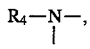, where $R_4$ is hydrogen, $C_1$–$C_8$alkyl, cyclohexyl or a group of formula (II), or $R_2$ is also one of the groups of formulae (IVa)–(IVc), in which $A_2$ is —$CH_2CH_2$— or —CO— and p is zero or 1;

$R_3$ is a group of formula (V) or a 4-morpholinyl group or an $R_5$O— or

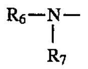

group, where $R_5$ is $C_1$–$C_4$alkyl and $R_6$ and $R_7$, which are identical or different, are hydrogen, $C_1$–$C_4$alkyl or cyclohexyl;

$G_1$ is a group of formula (VI), in which $A_3$ is a >N—($R_8$—$A_5$)$_q$— or

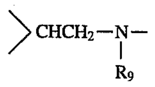

group, where $R_8$ is $C_2$–$C_3$alkylene, $A_5$ is —O— or

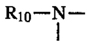

and q is zero or 1, $R_9$ and $R_{10}$ have any one of the meanings given for $R_4$ and $A_4$ is —$CH_2CH_2$— or, if $A_3$ is >N—, $A_4$ is also a

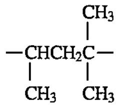

group;

$G_2$ is a group of formula (VII) in which $R_{11}$ has any one of the meanings given for $R_4$, $R_{12}$ is $C_2$–$C_6$alkylene, $C_6$–$C_{10}$alkylene interrupted by 2 or 3 oxygen atoms, cyclohexylenedimethylene or methylenedicyclohexylene, $A_6$ is as defined above for $A_5$ and m is 1, 2, 3 or 4;

if m is 1, $L_1$ is hydrogen, $C_1$–$C_8$alkyl, allyl, benzyl, aliphatic $C_1$–$C_8$acyl or ($C_1$–$C_8$alkoxy)carbonyl;

if m is 2, $L_1$ is $C_2$–$C_6$alkylene, $C_4$–$C_6$alkylene interrupted by 1 or 2 oxygen atoms, aliphatic $C_2$–$C_{12}$diacyl or one of the groups of formulae (VIIIa)-(VIIId), in which $R_{13}$ and $R_{14}$ have any one of the meanings given for $R_3$ or are a group of formula (IX), where $R_{18}$ is a group of formula (VI) or (VII), $R_{15}$ is a group of formula (Xa) or (Xb), in which $A_7$, $A_8$ and $A_9$, which are identical or different, are an

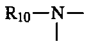

group, $R_{19}$ has any one of the meanings given for $R_{12}$, $R_{20}$ is $C_2$–$C_3$alkylene, s is zero or 1, $A_{10}$ has any one of the meanings given for $A_3$, $R_6$ and $R_{17}$ are $C_2$–$C_6$alkylene, $C_4$–$C_6$alkylene interrupted by 1 or 2 oxygen atoms, isopropylidenedicyclohexylene or isopropylidenediphenylene and r is zero or 1;

if m is 3, $L_1$ is a group of formula (XIa) or (XIb), in which $R_{24}$ is as defined above for $R_{14}$ and $R_{25}$ is a group of formula (XIIa) or (XIIb), in which t is zero, $A_{11}$ and $A_{12}$ are an

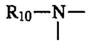

group, $R_{26}$ and $R_{27}$, which are identical or different, are $C_2$–$C_3$alkylene, $R_{29}$, $R_{30}$ and $R_{31}$ have any one of the meanings given for $R_4$, $A_{14}$ is a direct bond or —$CH_2$— and u and v, which are identical or different, are integers from 3 to 5;

if m is 4, $L_1$ is a group of formula (XIII), in which $R_{34}$ is as defined above for $R_{14}$ and $R_{35}$ is group of formula (XIVa), in which $A_{15}$ is an

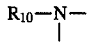

group, $R_{36}$ and $R_{37}$, which are identical or different, are $C_2$–$C_3$alkylene and x is zero;

n is 2, 3 or 4 and, if n is 2, $L_2$ is one of the groups of formulae (VIIIb)-(VIIId) as defined above;

if n is 3, $L_2$ is a group of formula (XIa) or (XIb) as defined above and, if n is 4, $L_2$ is a group of formula (XIII) as defined above.

Compounds of formula (Ia) or (Ib) of particular interest are those in which $R_1$ is hydrogen or methyl; $R_2$ is —O— or

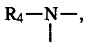

where $R_4$ is hydrogen, $C_1$–$C_4$alkyl or a group of formula (II), or $R_2$ is also a group of formula (IVa), in which $A_2$ is —$CH_2CH_2$— or —CO— and p is zero or 1; $R_3$ is a group of formula (V); $G_1$ is a

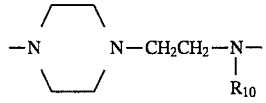

group; $G_2$ is a

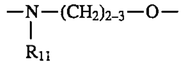

group and $R_{10}$ and $R_{11}$ have any one of the meanings given for $R_4$;

m is 2, 3 or 4 and, if m is 2, $L_1$ is aliphatic $C_2$–$C_{10}$diacyl or one of the groups of formulae (VIIIa)—(VIIId), in which $R_{13}$ and $R_{14}$ are a group of formula (V), a 4-morpholinyl group or a group of formula (IX), where $R_{18}$ is a $G_1$ group, $R_{15}$ is a

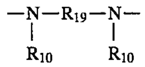

or

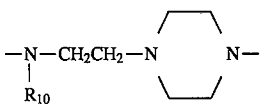

group, $R_{19}$ being —$(CH_2)_{2-6}$- or $C_8$–$C_{10}$alkylene interrupted by 2 or 3 oxygen atoms, $R_{16}$ is —$(CH_2)_{4-6}$ and r is zero; if m is 3, $L_1$ is a group of formula (XIa) or (XIb), in which $R_{24}$ is as defined above for $R_{14}$ and $R_{25}$ is a

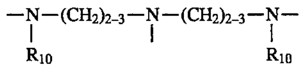

group; if m is 4, $L_1$ is a group of formula (XIII), in which $R_{34}$ is as defined above for $R_{14}$ and $R_{35}$ is a

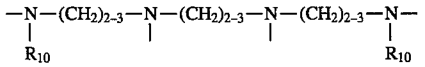

group of formula (VIIIb), in which $R_{14}$ is a group of formula (V) or a group of formula (IX), where $R_{18}$ is a $G_2$ group; if n is 3, $L_2$ is a group of formula (XIa), in which $R_{24}$ is a group of formula (V) or a group of formula (IX), where $R_{18}$ is a $G_2$ group and, if n is 4, $L_2$ is a group of formula (XIII), in which $R_{34}$ is a group of formula (V) or a group of formula (IX), where $R_{18}$ is a $G_2$ group.

The compounds of the present invention can be prepared in accordance with various processes known per se.

According to process A, compounds of formula (XVa) or (XVb)

(XVa)

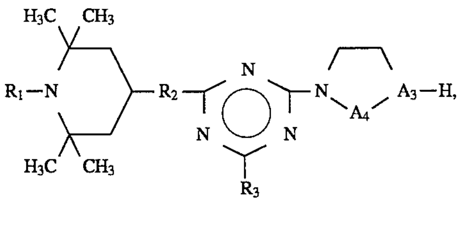

-continued

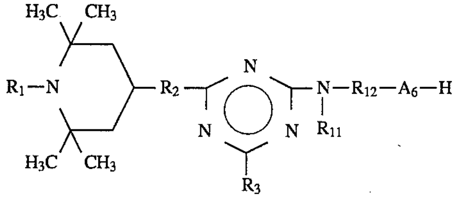

(XVb)

are first prepared by reaction of a compound of formula (XVIa) with a compound of formula (XVIb) or (XVIc)

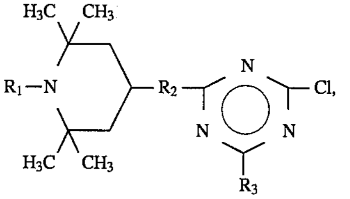

(XVIa)

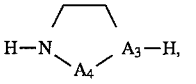

(XVIb)

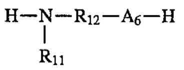

(XVIc)

Thereafter, the compounds of formula (XVa) or (XVb) are caused to react with appropriate molar amounts of suitable alkylating or acylating reagents.

According to process B, compounds of formula (XVIIa) or (XVIIb)

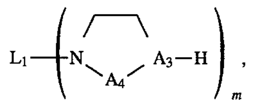

(XVIIa)

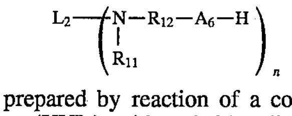

(XVIIb)

are first prepared by reaction of a compound of formula (XVIb) or (XVIc) with suitable alkylating or acylating reagents in the appropriate molar ratios.

Thereafter, the compounds of formula (XVIIa) or (XVIIb) are caused to react with the appropriate molar amounts of a compound of formula (XVIa).

The various reactions are advantageously carried out in an inert organic solvent, for example toluene, xylene or mesitylene, working at temperatures of from −20° to 200° C., preferably from 10° to 180° C.

The various stages of the reactions can be carried out in a single reactor and in the same reaction medium, without isolating the intermediate products, or can be carried out after their separation and, where appropriate, purification.

The reagents employed are commercially available or can be prepared in accordance with known processes.

The compounds of the present invention are highly effective in improving the light resistance, heat resistance and oxidation resistance of organic materials, in particular synthetic polymers and copolymers, and are particularly suitable for the stabilisation of polypropylene fibres, because of their high resistance to volatilisation.

Examples of organic materials which can be stabilised are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or ρ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (ssc).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but- 1-ene copolymers, propylene/isobutylene copolymers, ethylene/but-1-ene copolymers, ethylene/hexene copolymers, ethylene/methylpentene copolymers, ethylene/beptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylideneonorbornene; and mixtures of such copolymers with one another and with polymers mentioned in 1 ) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/ alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well ms mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1 ) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals ramified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-tximethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyelaoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The compounds of formula (I) are particularly suitable for improving the light stability, heat stability and stability to oxidation of Polyolefins, particularly polyethylene and polypropylene.

The compounds of formula (I) can be used in mixtures with organic materials in various proportions depending on the nature of the material to be stabilised, on the end use and on the presence of other additives.

In general, it is appropriate to use, for example, 0.01 to 5% by weight of the compounds of formula (I), relative to the weight of the material to be stabilised, preferably between 0.05 and 1%.

In general, the compounds of formula (D can be incorporated in the polymeric materials before, during or after the polymerisation or crosslinking of the said materials.

The compounds of formula (I) can be incorporated in the polymeric materials in the pure form or encapsulated in waxes, oils or polymers.

The compounds of formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilised with the products of formula (I) can be used for the production of mouldings, films, tapes, monofilaments, fibres, surface coatings and the like.

If desired, other conventional additives for synthetic polymers, such as antioxidants, UV absorbers, nickel stabilisers, pigments, fillers, plasticisers, antistatic agents, flame-proofing agents, lubricants, corrosion inhibitors and metal deactivators, can be added to the mixtures of the compounds of formula (I) with the organic materials.

Particular examples of additives which can be used in admixture with the compounds of formula (I) are:

1. Antioxidants 1.1. Alkylated monophenols, for example 2,6-di-tert-butyl-4-methylphenol, 2-tert-butyl- 4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α -methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6 -(1'-methylundec-1'-yl)phenol, 2,4-dimethyl-6-(1'-methylheptadec-1'-yl)phenol, 2,4 -dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6 -didodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6 -diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis( 6-tert-butyl-2-methylphenol), 4,4'-thiobis-(3,6-di-sec-amylphenol), 4,4'-bis-(2,6-dimethyl- 4-hydroxyphenyl) disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α -methylcyclohexyl)phenol], 2,2'-methylenebis(4-methyl-6-cyclohexylphenol), 2,2 '-methylenebis( 6-nonyl-4-methylphenol), 2,2'-methylenebis(4,6-di-tert-butylphenol), 2,2'-ethylidenebis( 4,6-di-tert-butylphenol), 2,2'-ethylidenebis(6-tert-butyl-4-isobutylphenol), 2,2'-methylenebis( 6-(α-methylbenzyl)-4-nonylphenol], 2,2'-methylenebis[6-(α,α-dimethylbenzyl)- 4-nonylphenol], 4,4'-methylenebis(2,6-di-tert-butylphenol), 4,4'-methylenebis(6 -tert-butyl-2-methylphenol), 1,1-bis(5-tert-butyl-4-hydroxy-2-methylphenyl)butane, 2,6-bis(3 -tert-butyl-5-methyl-2-hydroxybenzyl)-4-methylphenol, 1,1,3-tris(5-tert-butyl-4-hydroxy- 2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3 -tert-butyl-4-hydroxy-5-methyl-phenyl)dicyclopentadiene, bis[2-(3'-tert-butyl-2'-hydroxy- 5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5 -tert-butyl-4-hydroxy2-methylphenyl)-4-n-dodecylmercaptobutane, 1,1,5,5-tetra-(5 -tert-butyl-4-hydroxy2-methylphenyl)pentane.

1.6. O, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5 -di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2 -hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[ 4-( 1,1,3,3-tetramethylbutyl)phenyl]-2,2-bis( 3,5-di-tert-butyl-4-hydroxybenzyl)malonate.

1.8. Aromatic hydorxybenzyl compounds, for example 1,3,5-tris-(3,5-di-tert-butyl-4 -hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl-4 -hydroxyanilino)-1,3,5-triazine, 2-octylmercapto-4,6-bis(3,5-di-tert-butyl-4 -hydroxyanilino)-1,3,5-triazine, 2-octylmercapto-4,6-bis(3,5-di-tert-butyl-4-hydroxyphenoxy)- 1,3,5-triazine, 2,4,6-tris(3,5-di-tert-butyl-4-hydroxyphenoxy)- 1,2,3-triazine, 1,3,5-tris-( 3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5 -di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)propionic acid with mono-or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl-)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5-dicyclohexyl-4-hydroxyphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.21octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanecliol, trimethylolpropane, 4-hydroxymethyl-1-phospha-2,6,7-trioxabicyclo [2.2.2]octane.

1.16. Amides of β-(3,5-di-tert-butyl-4-hydroxyphenyl)propionic acid e.g. N,N'-bis(3,5 -di-tert-butyl-4-hydroxyphenylpropionyl)hexamethylenediamine, N,N'-bis(3,5-di-tert-butyl- 4-hydroxyphenylpropionyl)trimethylenediamine, N,N'-bis(3,5-di-tert-butyl-4 -hydroxyphenylpropionyl)hydrazine.

2. UV absorbers and light stabilisers 2.1.2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2' -hydroxyphenyl)benzotriaze, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3 '-tert-butyl- 2-hydroxy-5-methylphenyl)-5-chloro-benzotriazole, 2-(3-sec-butyl-5-tert-butyl-2-hydroxyphenyl)benzot 2-(2'-hydroxy-4'-octyloxyphenyl)benzotriazole, 2-(3',5' di-tert-amyl-2'-hydroxyphenyl)benzotriazole, 2-(3',5'-bis-(α, α-dimethylbenzyl)-2' -hydroxyphenyl)benzotriazole, mixture of 2-(3'-tert-butyl-2'-hydroxy-5'-(2 -octyloxycarbonylethyl)phenyl)-5-chloro-benzotriazole, 2-(3'-tert-butyl-5'-[2-(2-ethylhexyloxy)-carbonylethyl] -2'-hydroxyphenyl)-5-chloro-benzotriazole, 2-(3'-tert-butyl-2'-hydroxy-5'-(2 -methoxycarbonylethyl)phenyl)-5-chloro-benzotriazole, 2-(3'-tert-butyl-2'-hydroxy-5'-(2 -methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl] -2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-( 1,1,3,3-tetramethylbutyl)-6-benzotriazole-2-ylphenol]; the transesterification product of 2-[3'-tert-butyl-5'-(2-methoxycarbonylethyl)-2'-hydroxyphenyl] -2H-benzotriazole with polyethylene glycol 300; $[R—CH_2CH_2—COO(CH_2)_3]_2—$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4 -tert-butylbenzoyl) resorcinol, benzoyl resorcinol, 2,4-di-tertbutylphenyl 3,5-di-tert-butyl- 4-hydroxybenzoate, hexadecyl 3,5-di-tert-butyl-4-hydroxybenzoate, octadecyl 3,5-di-tert-butyl- 4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3 -tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4 -hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered mines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4 -piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6 -pentamethylpiperidyl)-2-n-butyl-2-(2-hydroxy-3,5-di-tert-butylbenzyl)malonate, 3-n-octyl- 7,7,9,9-tetramethyl-1,3,8-triazasprio[4.5] decan-2,4-dion, bis(1-octyloxy-2,2,6,6 -tetramethylpiperidyl)sebacate, bis(1-octyloxy-2,2,6,6-tetramethylpiperidyl)succinate, the condensate of N,N'-bis-(2, 2,6,6-tetramethyl-4-piperidyl)hexamethylenediamine and 4-morpholino-2,6-dichloro- 1,3,5-triazine, the condensate of 2-chloro-4,6-bis(4 -n-butylamino-2,2,6,6-tetramethylpiperidyl )-1,3,5-triazine and 1,2-bis(3-aminopropylamino)ethane, the condensate of 2-chloro-4,6-di-(4-n-butylamino-1, 2,2,6,6 -pentamethylpiperidyl)-1,3,5-triazine and 1,2-bis-(3-aminopropylamino)ethane, 8-acetyl-3-dodecyl-7,7,9,9 -tetramethyl-1,3,8-triazaspiro[4.5]decane-2,4-dione, 3-dodecyl-1-(2,2,6,6-tetramethyl-4 -piperidyl)pyrrolidin-2, 5-dione, 3-dodecyl-1-(1,2,2,6,6-pentamethyl-4 -piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis( 3-dimethylaminopropyl)oxamide, 2-ethoxy-5-tert-butyl-2'- ethoxanilide and its mixture with 2-ethoxy-2'-ethyl-5,4'-di-tert-butoxanilide and mixtures of ortho- and para- methoxy-disubstituted oxanilides and mixtures of o- and p-ethoxy-disubstituted oxanilides.

2.8. 2-(2-Hydroxyphenyl)-1,3,5-triazines, for example 2,4, 6-tris(2-hydroxy-4 -octyloxyphenyl)-1,3,5-triazine, 2-(2-hydroxy-4-octyloxyphenyl)-4,6-bis(2,4-dimethylphenyl)- 1,3, 5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)- 1,3,5-triazine, 2-(2 -hydroxy-4-octyloxyphenyl)-4,6-bis(4-methylphenyl)-1,3,5-triazine, 2-(2-hydroxy-4 -dodecyloxyphenyl)-4,6-bis(2,4-dimethylphenyl)-1,3,5-triazine, 2-[2-hydroxy-4-(2hydroxy- 3-butyloxy-propoxy)phenyl]-4,6-bis(2,4-dimethyl)-1,3,5-triazine, 2-[2-hydroxy-4-(2 -hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis-(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaeryt hritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyl-oxy- 2,4,8,10-tetra-tert-butyl-12H-dibenz[d,g]- 1,3,2-dioxaphosphocin, 6-fluoro-2,4,8,10 tetra-tert-butyl-12-methyl-dibenz[d,g]- 1,3,2-dioxaphosphocin, bis(2,4-di-tert-butyl-6-methylphenyl)methylphosphite bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N,N-dialkylhydroxylamine derived from hydrogenated tallow amine.

7. Polyamide stabilisers, for example, copper salts in combination with iodides and/or phosphorus compounds and salts of divalent manganese.

8. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium riciholeate and potassium palmitate, antimony pyrocatecholate or tin pyrocatecholate.

9. Nucleating agents, for example, 4-tert-butylbenzoic acid, adipic acid, diphenylacetic acid.

10. Fillers and reinforcing agents, for example, calcium carbonate, silicates, glass fibres, asbestos, talc, kaolin, mica, barium sulfate, metal oxides and hydroxides, carbon black, graphite.

11. Other additives, for example, plasticisers, lubricants, emulsifiers, pigments, optical brighteners, flameproofing agents, antistatic agents and blowing agents.

12. Benzofuranones and indolinones, for example those disclosed in U.S. Pat. Nos. 4,325,863, 4,338,244 or 5,175, 312, or 3-[4-(2-acetoxyethoxy)phenyl]-5,7 -di-tert-butyl-benzofuran-2-one, 5,7-di-tert-butyl-3-[4-(2-stearoyloxy-ethoxy)phenyl]benzofuran-2-one, 3,3'-bis[5,7-di-tert-butyl-3-(4-[2-hydroxyethoxy]phenyl)benzofuran-2-one], 5,7 -di-tert-butyl-3-(4-ethoxyphenyl)benzofuran-2-one, 3-(4-acetoxy-3,5-dimethylphenyl)-5,7 -di-tert-butyl-benzofuran-2-one, 3-(3,5-dimethyl-4-pivaloyloxyphenyl)-5,7 -di-tert-butyl-benzofuran-2-one.

The compounds of the formula (I) can also be used as stabilizers, especially as light stabilizers, for almost all materials known in the art of photographic reproduction and other reproduction techniques as e.g. described in Research Disclosure 1990, 31429 (pages 474 to 480).

In order to illustrate the present invention more clearly, there will now be described some examples of the preparation and of the use of the compounds of formulae (Ia) and (Ib); these examples are given purely by way of illustration and do not imply any limitation.

EXAMPLE 1

Preparation of the compound of formula

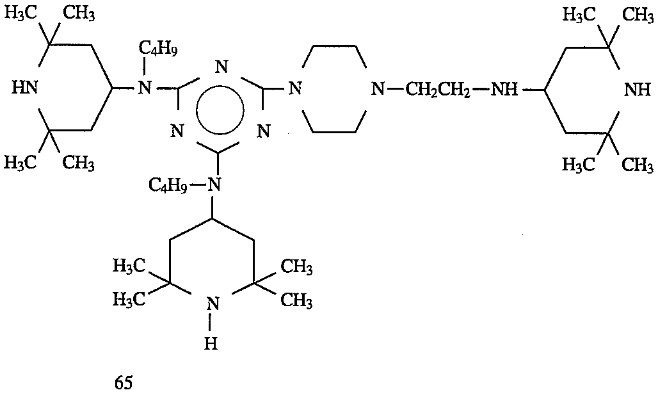

A solution of 321.7 g (0.6 mol) of N,N'-dibutyl-6-chloro-N,N'-bis(2,2,6,6-tetramethyl- 4-piperidyl)-1,3,5-triazine-2,4-diamine in 600 ml of xylene is added, over 2 hours, to a mixture, heated to 90° C., of 161.1 g (0.6 mol) of N-(2,2,6,6-tetramethyl-4-piperidyl)- 1-piperazine-ethanamine, dissolved in 600 ml of xylene, and 24 g (0.6 mol) of sodium hydroxide, dissolved in 80 ml of water. After completion of the addition, the mixture is heated to the boil for 1 hour and under reflux for 4 hours, with azeotropic removal of the water.

After cooling to 70° C., the reaction mixture is washed twice with 200 ml of water, heated under reflux with azeotropic removal of the residual water, and evaporated in vacuo. The residue is crystallised from octane.

The product obtained melts at 128°–130° C.

Analysis for $C_{44}H_{85}N_{11}$

Calculated: C=68.79%; H=11.15%; N=20.06%

Found: C=68.67%; H=11.05%; N=19.96%

$^1$H NMR (60 MHz, $CDCl_3$): δ 2.3 ppm (m, 9H,

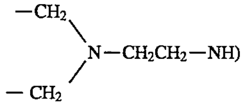

EXAMPLE 2

The compound of formula

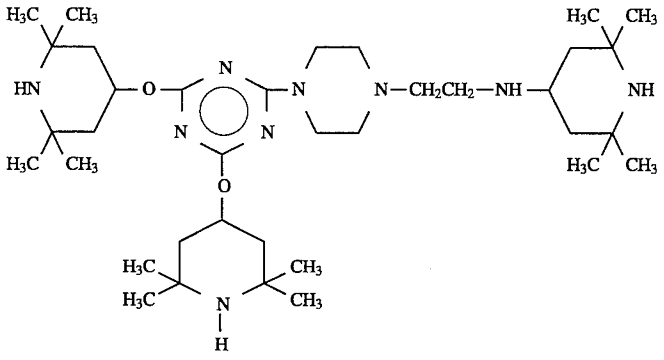

is prepared as described in Example 1, by reaction of 85.2 g (0.2 mol) of 2-chloro-4,6-bis(2,2,6,6-tetramethyl-4-piperidyloxy)-1,3,5-triazine with 53.7 g (0.2 mol) of N-(2,2,6,6-tetramethyl-4-piperidyl)-1-piperazine-ethanamine.

The product obtained melts at 1 11°–113° C. after crystallisation from octane.

Analysis for $C_{36}H_{67}N_9O_2$

Calculated: C=65.72%; H=10.26%; N=19.16%

Found: C=65.29%; H=10.20%; N=19.19%

$^1$H NMR (60 MHz, $CDCl_3$): δ 2.3 ppm (m, 9H,

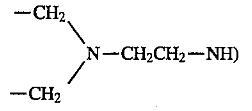

In the following examples 3–7 the preparation of some starting materials for compounds according to the instant invention is demonstrated.

EXAMPLE 3

Preparation of the compound of formula

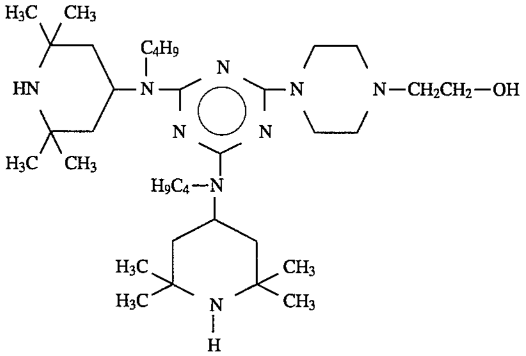

A mixture of 26 g (0.2 mol) of 1-piperazine-ethanol, 107.2 g (0.2 mol) of N,N'-dibutyl- 6-chloro-N,N'-bis(2,2,6,6-tetramethyl-4-piperidyl)- 1,3,5-triazine-2,4-diamine, 30.4 g (0.22 mol) of ground potassium carbonate and 400 ml of xylene is heated under reflux for 10 hours, with azeotropic removal of the water of reaction.

After cooling to 40° C., the reaction mixture is filtered, washed with water, dried over anhydrous $Na_2SO_4$ and evaporated in vacuo.

The product obtained melts at 137°–139° C.

Analysis for $C_{35}H_{67}N_9O$

Calculated: C=66.73%; H=10.72%; N=20.01%

Found: C=66.69%; H=10.71%; N=20.03%

EXAMPLE 4

The compound of formula

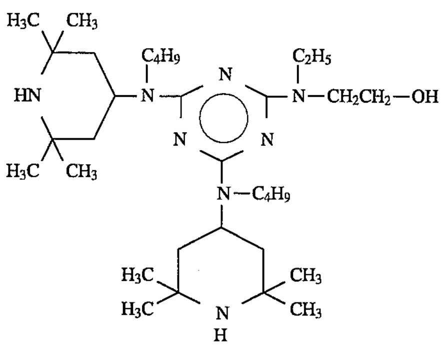

is prepared as described in Example 3, by reaction of 107.2 g (0.2 mol) of N,N'-dibutyl-6-chloro-N,N'-bis(2,2,6,6-tetramethyl-4-piperidyl)-1,3,5-triazine-2,4-diamine with 17.8 g (0.2 mol) of N-ethyl ethanolamine.

The product obtained melts at 93°–95° C.

Analysis for $C_{33}H_{64}N_8O$

Calculated: C=67.30%; H=10.95%; N=19.03%

Found: C=67.18%; H=10.94%; N=18.95%

EXAMPLE 5

The compound of formula

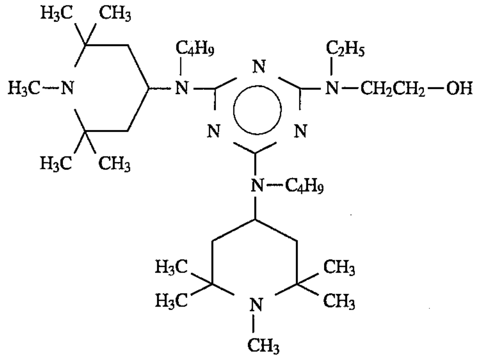

is prepared as described in Example 3, by reaction of 112.9 g (0.2 mol) of N,N'-dibutyl-6 -chloro-N,N'-bis(1,2,2,6,6-pentamethyl-4-piperidyl)-1,3,5-triazine-2,4-diamine with 17.8 g (0.2 mol) of N-ethyl ethanolamine.

The product obtained melts at 57°–59° C.

Analysis for $C_{35}H_{68}N_8O$

Calculated: C=68.14%; H=11.11%; N=18.16%

Found: C=68.40%; H=11.10%; N=18.05%

EXAMPLE 6

The compound of the formula

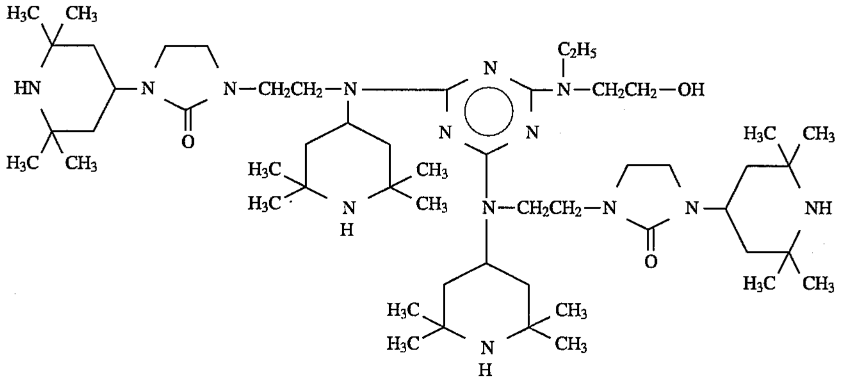

is prepared as described in Example 3, by reaction of 96.3 g (0.1 mol) of 6 -chloro-N,N'-bis(2,2,6,6-tetramethyl-4-piperidyl)-N,N'-bis[1-(2-aminoethyl)-3-(2,2,6,6 -tetramethyl-4-piperidyl)-2-imidazolidinone]-1,3,5-triazine-2,4-diamino with 8.9 g (0.1 mol) of N-ethyl ethanolamine.

The product obtained melts at 138°–140° C.

Analysis for $C_{53}H_{98}N_{14}O_3$

Calculated: C=64.99%; H=10.09%; N=20.02%

Found: C=64.58%; H=10.02%; N=19.92%

EXAMPLE 7

The compound of formula

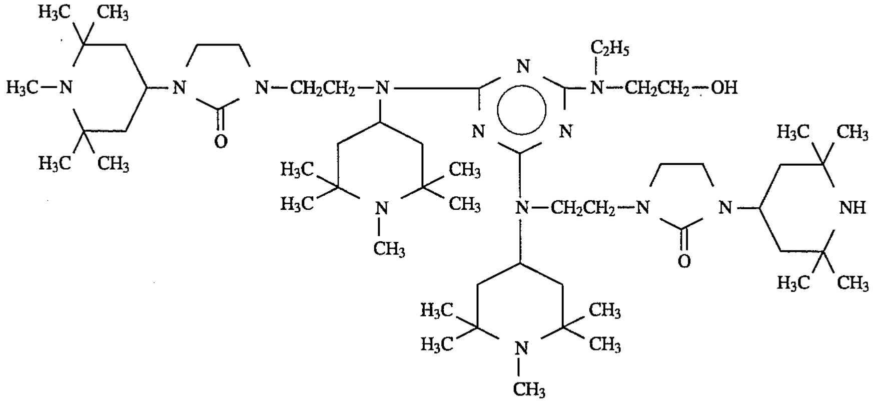

is prepared as described in Example 3, by reaction of 101.9 g (0.1 mol) of 6-chloro-N,N'-bis( 1,2,2,6,6-pentamethyl-4-piperidyl)-N,N'-bis[1-(2-aminoethyl)-3-( 1,2,2,6,6 -pentamethyl-4-piperidyl)-2-imidazolidinone]-1,3,5-triazine-2,4-diamine with 8.9 g (0.1 mol) of N-ethyl ethanolamine.

The product obtained melts at 146°–148° C.

Analysis for $C_{57}H_{106}N_{14}O_3$

Calculated: C=66.11%; H=10.22%; N=18.94%

Found: C=66.15%; H=10.33%; N=18.97%

EXAMPLE 8

Preparation of the compound of formula

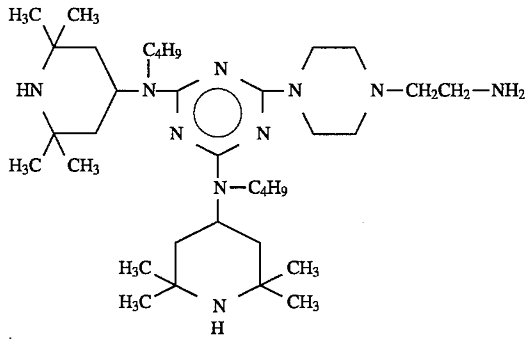

A solution of 321.7 g (0.6 mol) of N,N'-dibutyl-6-chloro-N,N'-bis(2,2,6,6-tetramethyl- 4-piperidyl)-1,3,5-triazine-2,4-diamine in 600 ml of xylene is added, over 2 hours, to a mixture, heated to 60° C. of 116.3 g (0.9 mol) of 1-piperazineethanamine dissolved in 250 ml of xylene and 24 g (0.6 mol) of sodium hydroxide dissolved in 80 ml of water. After completion of the addition, the mixture is heated at 60° C. for 1 hour, washed twice with 300 ml of water, dried over sodium sulfate and filtered.

The product is obtained by crystallization from xylene and melts at 71°–73° C.

Analysis for $C_{35}H_{68}N_{10}$

Calculated: C=66.83%; H=10.90%; N=22.27%

Found: C=66.84%; H=10.88%; N=22.22%

$^1$H NMR (60 Mhz, $CDCl_3$): 3.7 ppm(t,4H

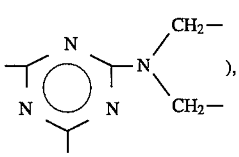

), 2.8 ppm (m, 2H —$CH_2$—($NH_2$)).

EXAMPLE 9

The compound of formula

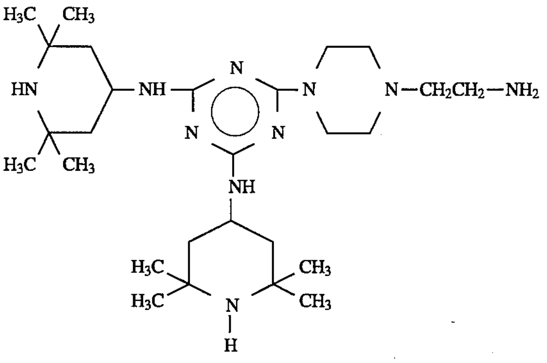

is prepared as described in Example 8, by reaction of 84.8 g (0.2 mol) of 6-chlor-N,N'-bis-( 2,2,6,6-tetramethyl-4-piperidyl)-1,3,5-triazine-2,4-diamine with 38.8 g (0.3 mol) of 4-piperazineethanamine.

The product obtained melts at 84°–86° C.

Analysis for $C_{27}H_{52}N_{10}$

Calculated: C=62.75%; H=10.14%; N=27.10%

Found: C=62.61%; H=10.08%; N=27.02%

$^1$H NMR (60 Mhz, $CDCl_3$): 3.7 ppm (t, 4H

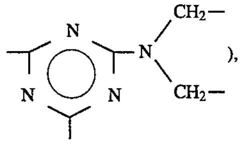

), 2.8 ppm (m, 2H, —$CH_2$—($NH_2$)).

EXAMPLE 10

The compound of formula

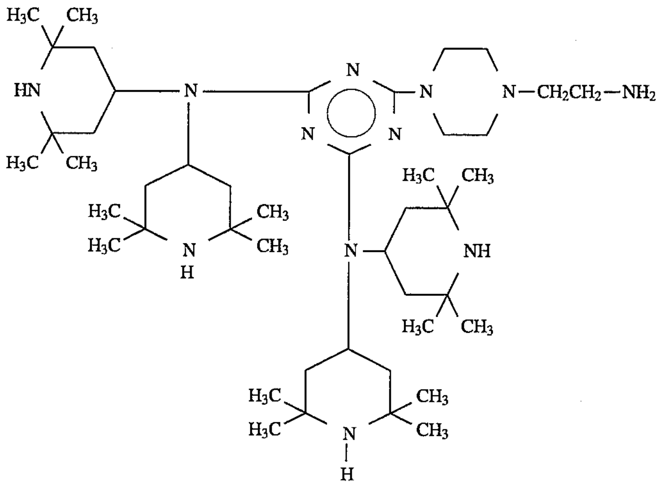

is prepared as described in Example 8, by reaction of 70.2 g (0.1 mol) of 6-chloro-N,N'tetrakis( 2,2,6,6-tetramethyl-4-piperidyl)-1,3,5-triazine-2,4-diamine with 19.4 g (0.15 mol) of 1-piperazineethanamine.

The product obtained melts at 252°–254° C.

Analysis for $C_{45}H_{86}N_{12}$

Calculated: C=67.96%; H=10.90%; N=21.14%

Found: C=67.52%; H=10.81%; N=20.99%

$^1$H NMR (60 Mhz, $CDCl_3$): 3.7 ppm (t, 4H

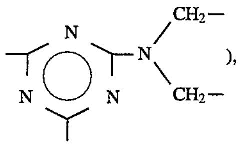

2.8 ppm (m, 2H —$CH_2$—($NH_2$)).

EXAMPLE 11

The compound of formula

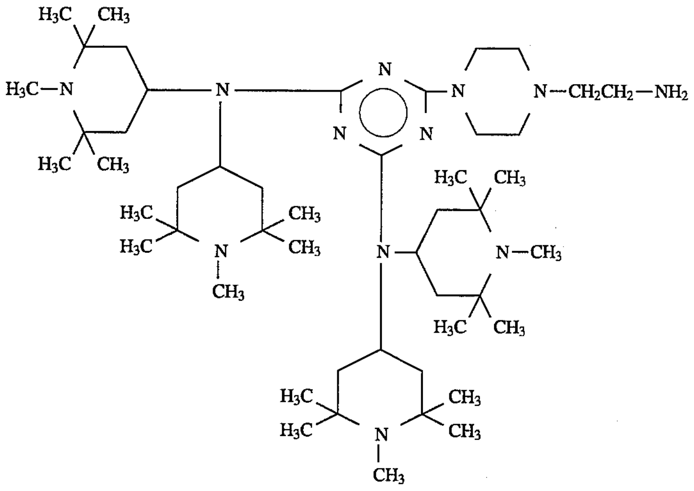

is prepared as described in Example 8, by reaction of 75.9 g (0.1 mol) of 6-chloro-N,N'-tetrakis(1,2,2,6,6-pentamethyl-4-piperidyl)-1,3,5-triazine-2,4-diamine with 19.4 g (0.15 mol) of 1-piperazineethanamine.

The product obtained melts at 261°–263° C.

Analysis for $C_{49}H_{94}N_{12}$

Calculated: C=69.13%; H=11.13%; N=19.74%

Found: C=69.08%; H=11.06%; N=19.80%

$^1$H NMR (60 Mhz, $CDCl_3$): 3.7 ppm (t, 4H

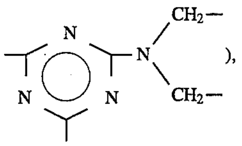

2.8 ppm (m, 2H—$CH_2$—($NH_2$)).

EXAMPLE 12

Preparation of the compound of formula

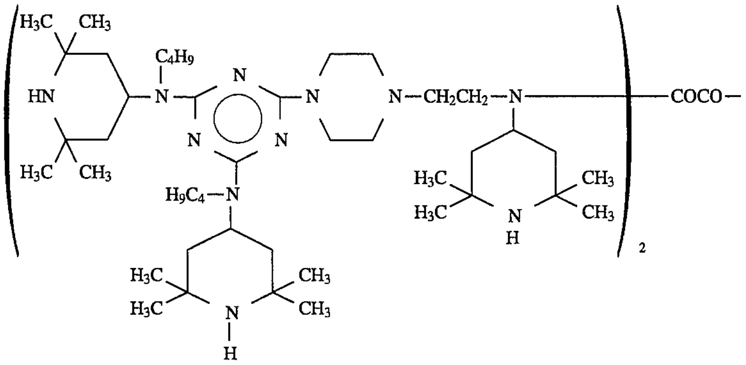

A solution of 1.76 g (0.0139 mol) of oxalyl chloride in 20 ml of 1,2-dichloroethane is added slowly to a solution of 20 g (0.026 mol) of the compound of Example 1 in 100 ml of 1,2-dichloroethane, whilst keeping the temperature at −5° C. After completion of the addition, the mixture is stirred for I hour at 0° C. and for 2 hours at ambient temperature. It is cooled to 0° C., a solution of 1.2 g (0.03 mol) of sodium hydroxide in 10 ml of water is added whilst maintaining the abovementioned temperature, and the mixture is then stirred for 2 hours at ambient temperature. The organic phase is separated off, dried over anhydrous $Na_2SO_4$ and evaporated in vacuo. The residue is crystallised from hexane.

The product obtained melts at 132°–134° C.

Analysis for $C_{90}H_{168}N_{22}O_2$

Calculated: C=67.97%; H=10.65%; N=19.37%

Found: C=67.90%; H=10.67%; N=19.31%

EXAMPLES 13–14

Following the process described in Example 12, and using the respective reagents in the appropriate molar ratios, the following compounds of formula

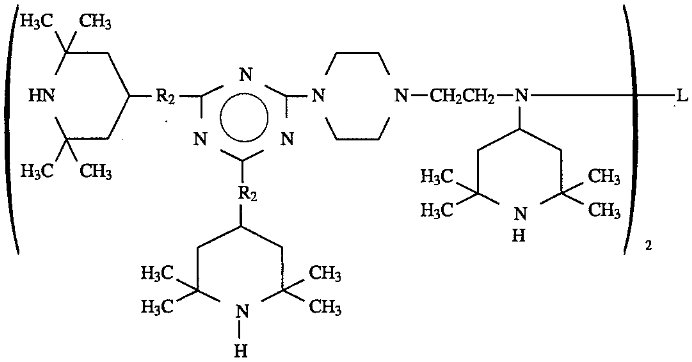

are prepared.

| Example | $R_2$ | L | Melting point (°C.) |
|---|---|---|---|
| 13 | 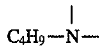 | 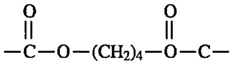 | 106–108 |
| 14 | —O— | 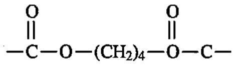 | 63-65 |

EXAMPLE 15

Preparation of the compound of formula

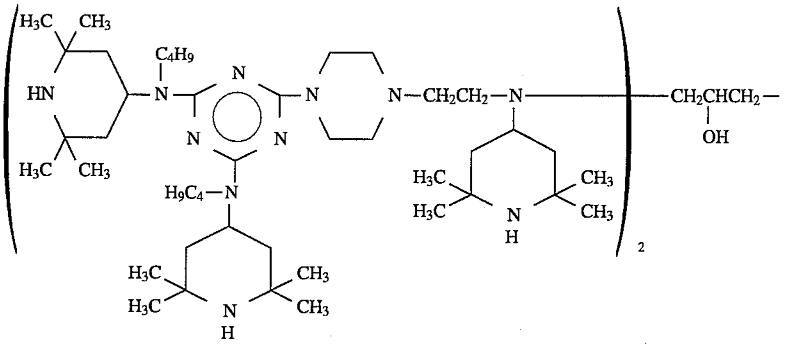

A solution of 1.3 g (0.0139 mol) of epichlorohydrin in 10 ml of 2-methyl-2-butanol is added to a solution, heated to 60° C., of 20 g (0.026 mol) of the compound of Example 1 in 100 ml of 2-methyl-2-butanol. The mixture is heated for 2 hours at 80° C. and for 3 hours under reflux, with 0.6 g (0.015 mol) of ground sodium hydroxide being added a little at a time.

After cooling to 40° C., the reaction mixture is filtered and evaporated in vacuo and the residue is dissolved in 100 ml of toluene. The solution obtained is washed twice with water, dried over anhydrous $Na_2SO_4$ and evaporated in vacuo. A residue which solidifies slowly, and has a melting point of 68°–70° C., is obtained.

Analysis for $C_{91}H_{174}N_{22}O$

Calculated: C=68.63%; H=11.01%; N=19.35%

Found: C=69.00%; H=11.01%; N=19.33%

EXAMPLE 16

Preparation of the compound of formula

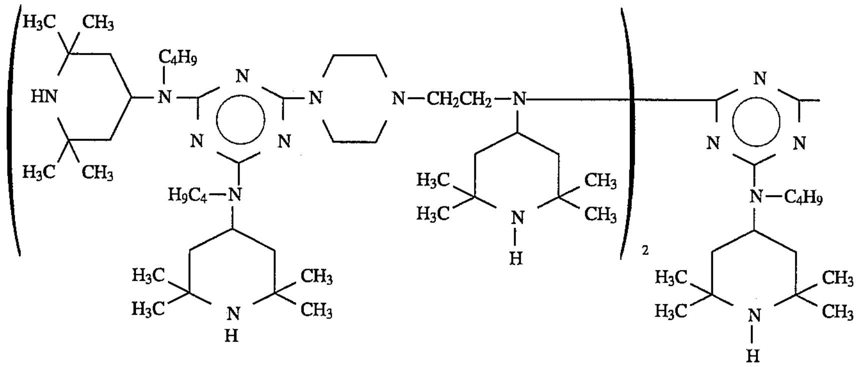

7.2 g (0.034 mol) of N-butyl-2,2,6,6-tetramethyl-4-piperidine-amine, dissolved in 30 ml of xylene, are added slowly to a solution of 6.3 g (0.034 mol) of cyanuric chloride in 50 ml of xylene, whilst keeping the temperature at between -5° and 0° C. The mixture is stirred for 2 hours at ambient temperature, a solution of 1.6 g (0.04 mol) of sodium hydroxide in 15 ml of water is added and the batch is stirred for 30 minutes at the same temperature.

The aqueous phase is separated off, 52.2 g (0.068 mol) of the compound of Example 1 are added and the mixture is heated for 2 hours under reflux. 4.1 g (0.102 mol) of ground sodium hydroxide are added arid the mixture is heated under reflux for 8 hours, with azeotropic removal of the water of reaction, and thereafter for a further 6 hours with removal of 20 ml of xylene.

After cooling to 70° C., the reaction mixture is diluted with 60 ml of xylene, filtered and evaporated in vacuo. The residue is crystallised from acetonitrile. The product obtained melts at 131°–133° C.

Analysis for $C_{104}H_{195}N_{27}$

Calculated: C=68.49%; H=10.78%; N=20.73%

Found: C=68.55%; H-10.73%; N=20.69%

EXAMPLE 17

Preparation of the compound of formula

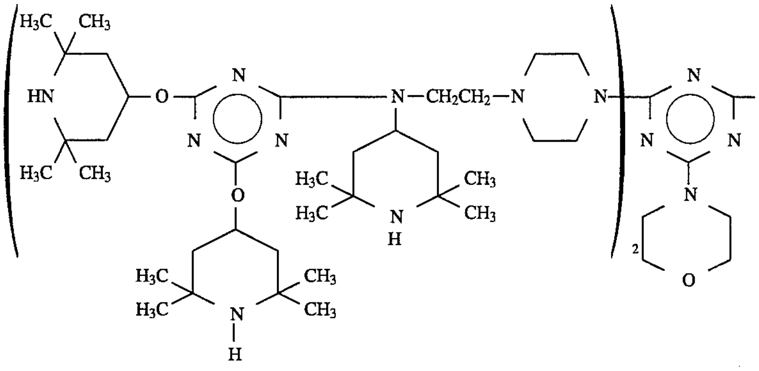

A solution of 23.5 g (0.1 mol) of 2,4-dichloro-6-morpholino-1,3,5-triazine in 80 ml of xylene is added, over 3 hours, to a solution, heated to 100°–110° C., of 53.7 g (0.2 mol) of N-(2,2,6,6-tetramethyl-4-piperidyl)-1-piperazine-ethanamine in 150 ml of xylene.

After completion of the addition, the mixture is heated to the boil for 1 hour, with addition of 16 g (0.4 mol) of ground sodium hydroxide, and is then heated under reflux for 8 hours, with azeotropic removal of the water of reaction.

After cooling to 60° C., 85.2 g (0.2 mol) of 2-chloro-4,6-bis(2,2,6,6-tetramethyl- 4-piperidyloxy)-1,3,5-triazine, 120 ml of xylene and 41.5 g (0.3 mol) of ground potassium carbonate are added and the mixture is heated under reflux for 10 hours with azeotropic removal of the water of reaction.

After cooling to 70° C., the reaction mixture is filtered and evaporated in vacuo.

The product obtained melts at 142°–145° C.

Analysis for $C_{79}H_{140}N_{22}O_5$

Calculated: C=64.19%; H=9.55%; N=20.85%

Found: C=64.0 1%; H=9.49%; N=20.75%

EXAMPLE 18

Preparation of the compound of formula

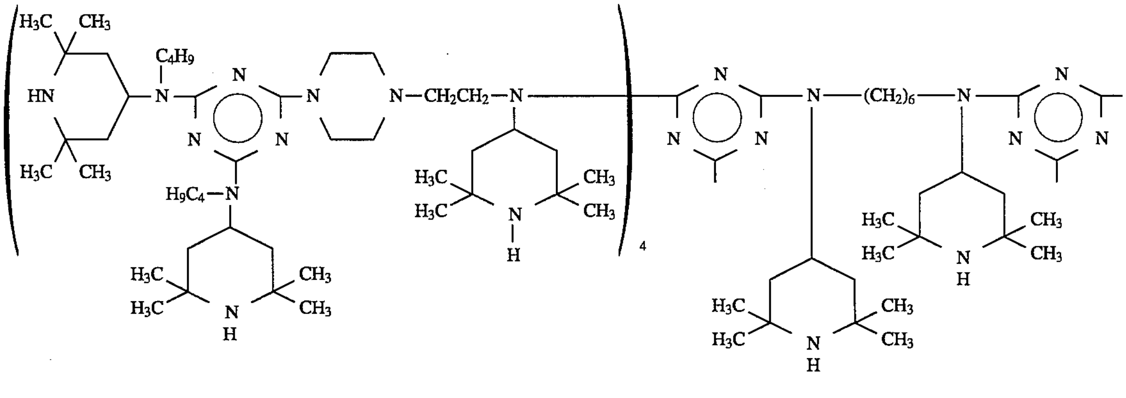

46.1 g (0.06 mol) of the compound of Example 1 are added to a solution, heated to 60° C., of 10.4 g (0.015 mol) of N,N'-bis(4,6-dichloro-1,3,5-triazin-2-yl)-N,N'-bis(2,2,6,6-tetramethyl-4-piperidyl)-1,6-hexanediamine in 100 ml of xylene. The mixture is heated at 80°–90° C. for 2 hours and is cooled to 60° C., and 3.6 g (0.09 mol) of ground sodium hydroxide are added. The mixture is then heated for 2 hours at 90° C., for 10 hours under reflux with azeotropic removal of the water of reaction and thereafter for a further 6 hours with removal of 40 ml of xylene.

After cooling to 70° C., the reaction mixture is diluted with 60 ml of xylene, filtered and evaporated in vacuo. The residue is crystallised from acetone.

The product obtained melts at 172°–174° C.

Analysis for $C_{206}H_{384}N_{54}$

Calculated: C=68.39%; H=10.70%; N=20.91%

Found: C=68.46%; H=10.70%; N=20.90%

EXAMPLES 19–22

Following the process described in Example 18 and using the respective reagents in the appropriate molar ratios, the following compounds of formula

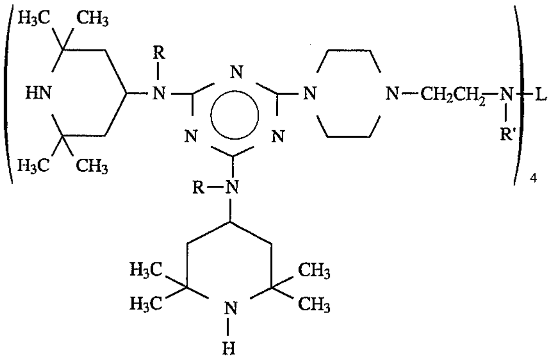
are prepared.
| Example | R | R' | L | melting point (C.°) |
|---|---|---|---|---|
| 19 | $-C_4H_9$ | 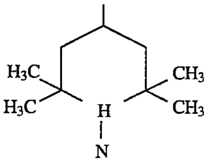 | 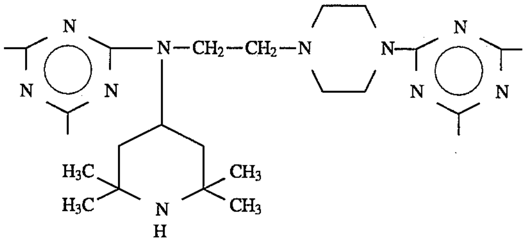 | 172–174 |
| 20 | $-C_4H_9$ | 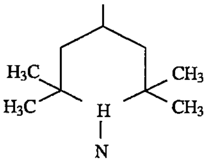 | 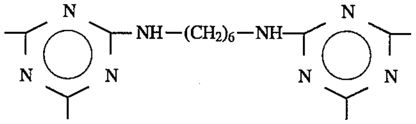 | 153–155 |
| 21 | $-C_4H_9$ | $-H$ | 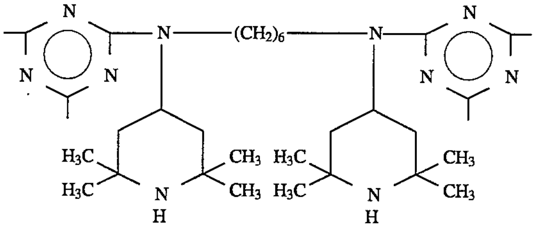 | 157–159 |
| 22 | 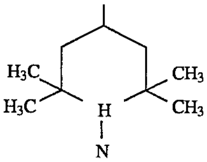 | $-H$ | 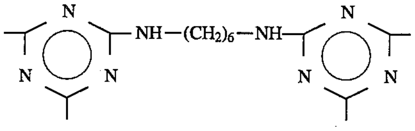 | 236–238 |
EXAMPLE 23
Preparation of the compound of formula

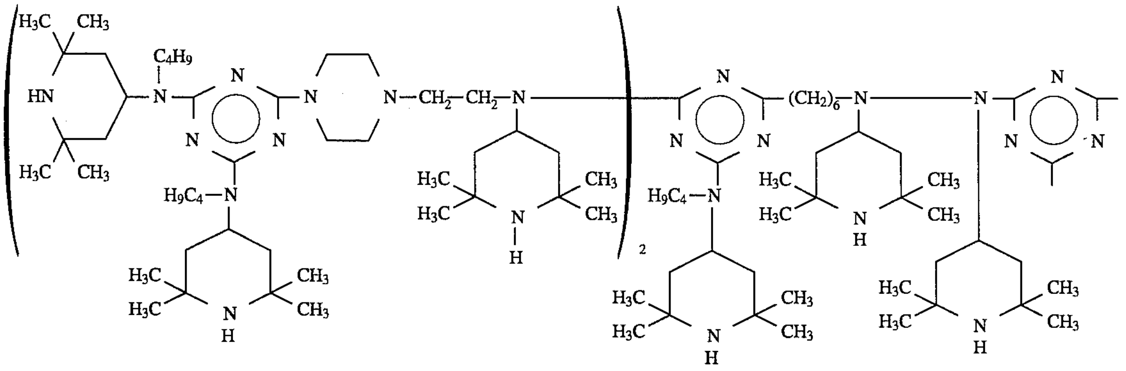

A solution of 6.4 g (0.03 mol) of N-butyl-2,2,6,6-tetramethyl-4-piperidine-amine in 20 ml of mesitylene is added to a solution, heated to 40° C., of 10.4 g (0.015 mol) of N,N'-bis(4,6-dichloro-1,3,5-triazin-2 -yl)-N,N'-bis(2,2,6,6-tetramethyl-4-piperidyl)-1,6-hexanediamine in 120 ml of mesitylene. The mixture is heated for 2 hours at 80° C., a solution of 1.2 g (0.03 mol) of sodium hydroxide in 20 ml of water is added, and the batch is heated further at 80°–90° C. for 3 hours.

The aqueous layer is separated off, 23.05 g (0.03 mol) of the compound of Example 1 are added and the mixture is heated under reflux for 1 hour. 2.4 g (0.06 mol) of ground sodium hydroxide are added and the mixture is heated under reflux for 12 hours, with azeotropic removal of the water of reaction. After cooling to 70° C., the reaction mixture is filtered and evaporated in vacuo.

The product obtained melts at 155°–157° C.

Analysis for $C_{144}H_{270}N_{36}$

Calculated: C=69.02%; H=10.86%; N=20.12%

Found: C=68.60%; H=10.78%; N=20.02%

EXAMPLE 24

Preparation of the compound of formula

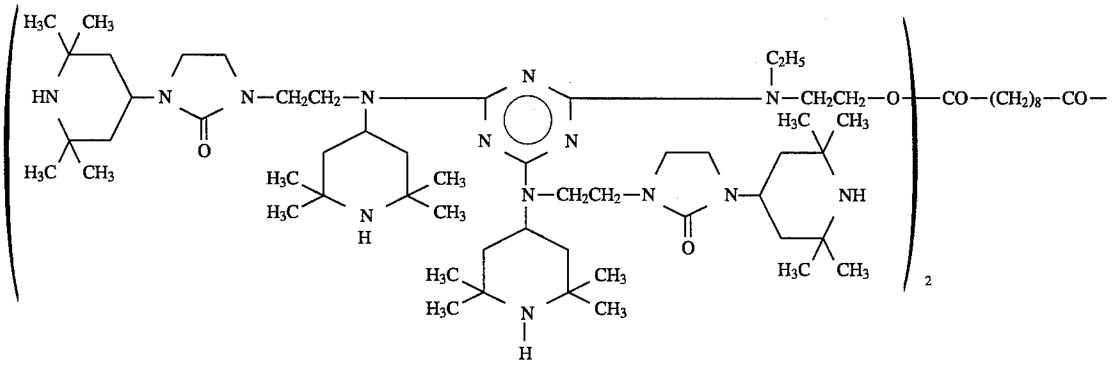

19.6 g (0.02 mol) of the compound of Example 6, 2.3 g (0.01 mol) of 1.10-decanedioic acid dimethyl ester and 100 ml of toluene are heated under reflux temperature with azeotropic removal of the possible water. The mixture is then added with 0.4 g of $LiNH_2$ and heated under reflux with removal of $CH_3OH$ of reaction for 4 hours. The mixture is cooled to room temperature, washed with water, dried over sodium sulfate and evaporated in vacuo.

The product obtained melts at 118°–121° C.

Analysis for $C_{116}H_{210}N_{28}O_8$

Calculated: C=65.56%; H=9.96%; N=18.45%

Found: C=65.28%; H=9.89%; N=18.38%

EXAMPLE 25

Preparation of the compound of formula

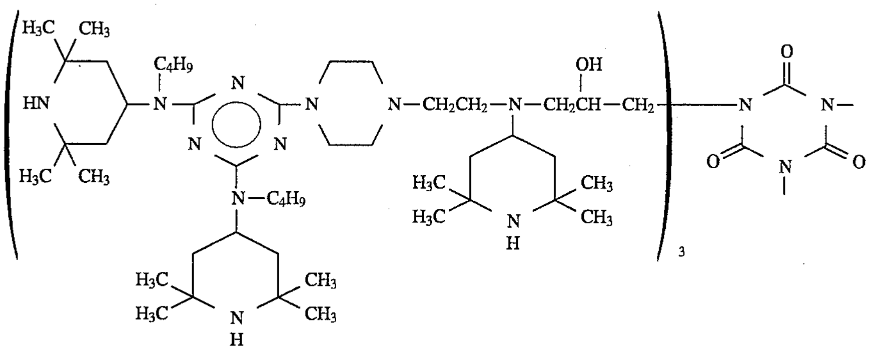

41.1 g (0.06 mol) of the compound of Example 1, 5.9 g (0.02 mol) of 1,3,5 -tris(oxiranylmethyl)-1,3,5-triazine-2,4,6(1H,3H,5H)-trione and 300 ml of t-amyl alcohol are heated under reflux for 18 hours. The mixture is then evaporated in vacuo, being the residue dissolved in 150 ml of xylene. The solution is washed with water, dried on sodium sulfate and evaporated in vacuo.

The product obtained melts at 148°–151° C.

Analysis for $C_{144}H_{270}N_{36}O_6$

Calculated: C=66.47%; H=10.46%; N=19.38%

Found: C=66.15%; H=10.38%; N=19.29%

EXAMPLE 26

Preparation of the compound of formula

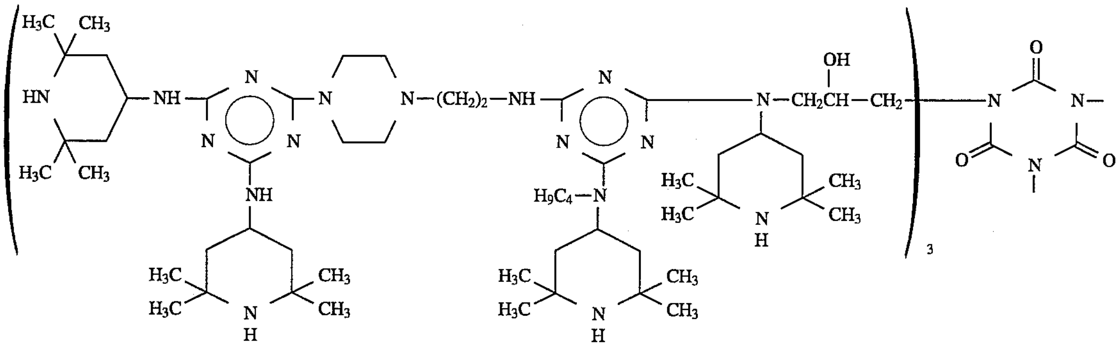

25.5 g (0.033 ml) of 1,3,5-tris[2-hydroxy-3-[(2,2,6,6-tetramethyl-4-piperidyl)amino] propyl] -1,3,5-triazine-2,4,6(1H,3H,5H)-trione, 36.0 g (0.1 mol)of N-butyl-4,6 -dichloro-N-(2,2,6,6-tetramethyl-4-piperidyl)-1,3,5-triazine-2-amine and 200 ml of xylene are heated to 90° C. for 2 hours. The mixture is then cooled to room temperature and added with 4.0 g (0.1 mol) of ground sodium hydroxide. The mixture is heated to 90° C. for 6 hours, cooled to room temperature and added with 51.7 g (0.1 mol) of the compound of Example 9. The mixture is heated to 120° C. for 2 hours, added with 4.8 g (0.12 mol) of ground sodium hydroxide and heated under reflux for 12 hours with azeotropic removal of the water of reaction and thereafter for further 6 hours with removal of 80 ml of xylene.

After cooling to 60° C., the reaction mixture is diluted with 80 ml of xylene, filtered and washed twice with 100 ml of water. The organic phase is separated off, dried on sodium sulfate, filtered and evaporated in vacuo. The residue is crystallized twice from acetonitrile.

The product obtained melts at 196°–199° C.

Analysis for $C_{168}H_{306}N_{54}O_6$

Calculated: C=63.48%; H=9.70%; N=23.79%

Found: C=63.26%; H=9.62%; N=23.29%

EXAMPLE 27

Preparation of the compound of formula

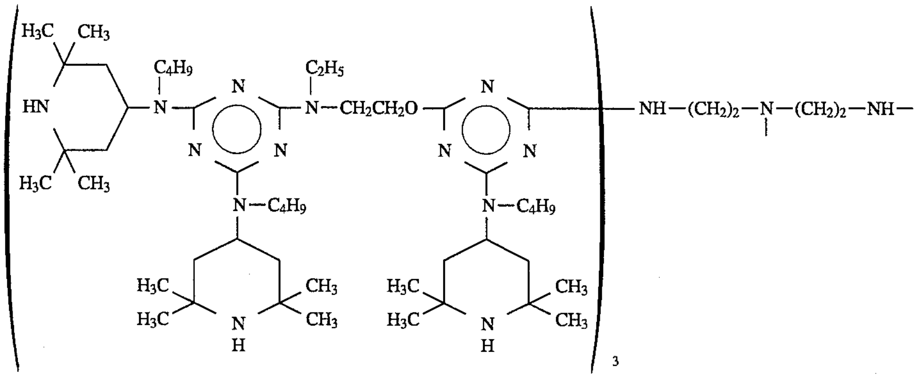

21.5 g (0.02 mol) of 1,4,7-tris[4-chloro-6-N-(2,2,6,6-tetramethyl-4-piperidyl)butylamino- 1,3,5-triazin-2-yl]-1,4,7-triazaheptane, 35.3 g (0.06 mol) of the compound of Example 4 and 150 ml of xylene are heated under reflux for 2 hours with azeotropic removal of the possible water. The mixture is cooled to 60° C. and added with 3.2 g (0.08 mol) of ground sodium hydroxide. The mixture is heated under reflux for 10 hours with azeotropic removal of the water of reaction and thereafter for further 4 hours with removal of 60 ml of xylene. After cooling to 60° C., the reaction is diluted with 60 ml of xylene, filtered and evaporated in vacuo. The residue is crystallized from acetonitrile.

The product obtained melts at 138°–140 C.

Analysis for $C_{154}H_{280}N_{42}O_3$

Calculated: C=66.38%; H=10.33%; N=21.53%

Found: C=66.12%; H=10.23%; N=21.41%

EXAMPLE 28

Preparation of the compound of formula

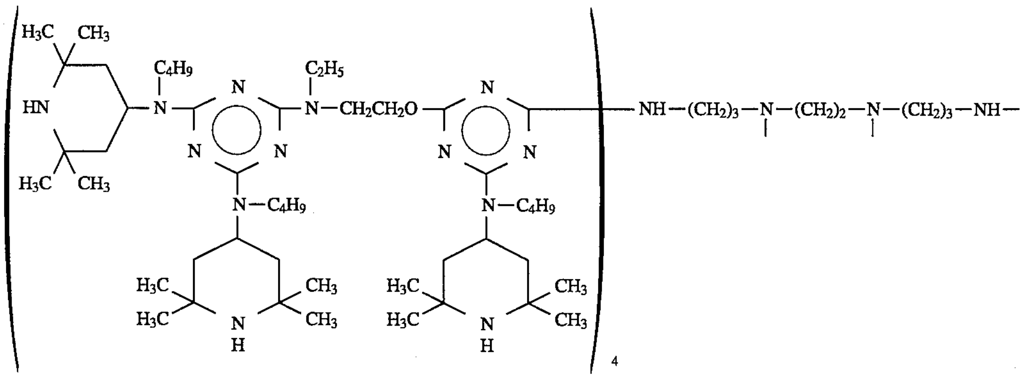

29.4 g (0.02 mol)of 1,5,8,12-tetrakis[4-chloro-6-N-(2,2,6,6-tetramethyl-4 -piperidyl)butylamino-1,3,5-triazin-2-yl]-1,5,8,12-tetraazadodecane, 42.1 g (0.08 mol) of the compound of Example 4 and 180 ml of xylene are heated under reflux for 2 hours with azeotropic removal of the possible water. The mixture is cooled to 60° C. and added with 4.2 g (0.105 mol) of ground sodium hydroxide. The mixture is heated under reflux for 10 hours with azeotropic removal of the water reaction and thereafter for further 6 hours with removal of 80 ml of xylene. After cooling to 60° C., the reaction is diluted with 80 ml of xylene, filtered and evaporated in vacuo.

The product obtained melts at 128°–130° C.

Analysis for $C_{204}H_{378}N_{56}O_4$

Calculated: C=66.59%; H=10.35%; N=21.32%

Found: C=66.24%; H=10.22%; N=21.03%

EXAMPLE 29

Preparation of the compound of formula

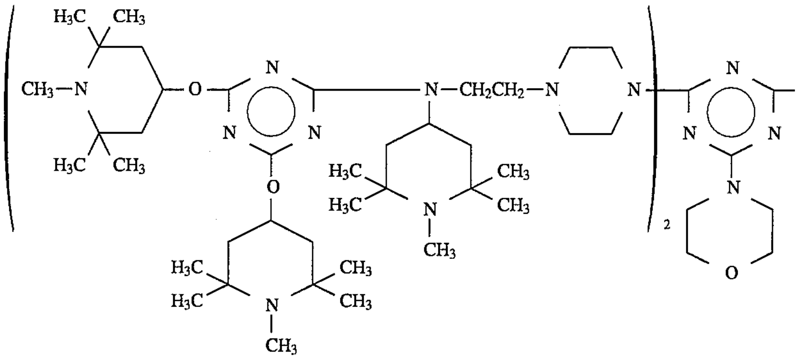

A solution containing 2. 16 g (0.072 mol) of formaldehyde and 3.30 g (0.072 mol) of formic acid in 8 ml of water is added, over 3 hours, to a solution, heated to 110° C., of 14.8 g (0.01 mol) of the compound of Example 17 in 60 ml of xylene, with simultaneous removal of the water.

After cooling to 70° C., a solution of 4.2 g (0.105 mol) of sodium hydroxide in 30 ml of water is added and the mixture is stirred for 30 minutes. The aqueous phase is separated off and the organic phase is washed with water, dried over anhydrous $Na_2SO_4$ and evaporated in vacuo.

The product obtained melts at 150°–153° C.

Analysis for $C_{85}H_{152}N_{22}O_5$

Calculated: C=65.35%; H=9.81%; N=19.72%

Found: C=65.26%; H=9.77%; N=19.71%

EXAMPLE 30

The compound of formula

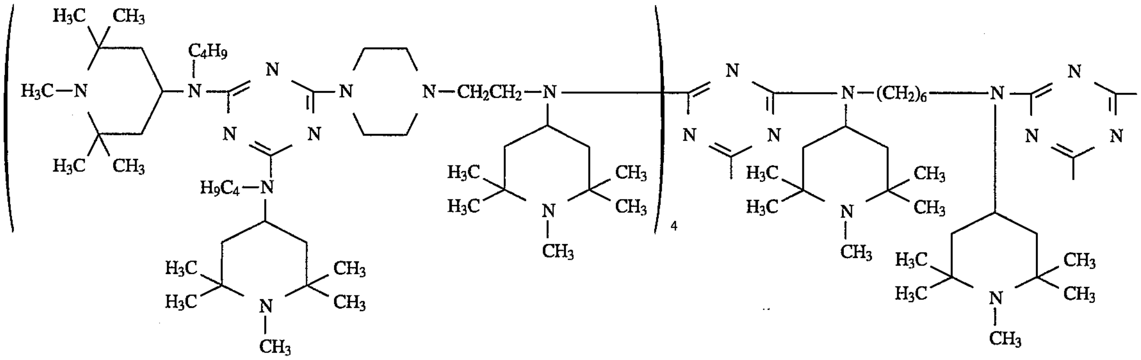

is prepared as described in Example 29, using the compound of Example 18.

The product obtained melts at 182°–184° C.

Analysis for $C_{220}H_{412}N_{54}$

Calculated: C=69.28%; H=10.89%; N=19.83%

Found: C=69.07%; H=10.81%; N=19.84%

EXAMPLE 31

The compound of formula

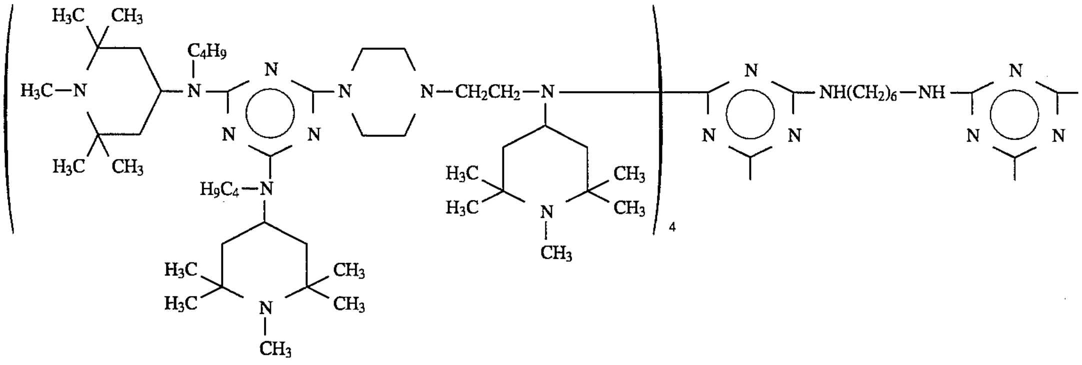

is prepared as described in Example 29, using the compound of Example 20.

The product obtained melts at 176°–179° C.

Analysis for $C_{200}H_{374}N_{52}$

Calculated: C=68.49%; H=10.75%; N=20.76%

Found: C=68.06%; H=10.70%; N=20.59%

EXAMPLE 32

The compound of formula

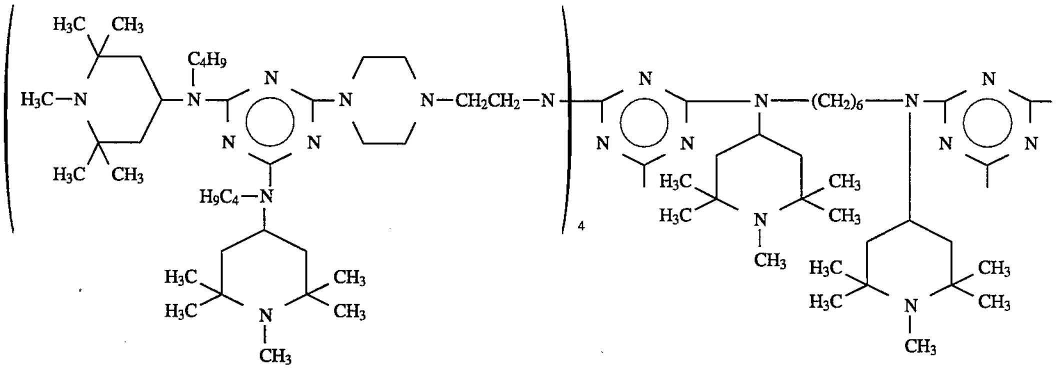

is prepared as described in Example 29, using the compound of Example 21.

The product obtained melts at 195–198 C.

Analysis for $C_{180}H_{336}N_{50}$

Calculated: C=67.54%; H=10.58%; N=21.88%

Found: C=67.05%; H=10.52%; N=21.49%

EXAMPLE 33

The compound of formula

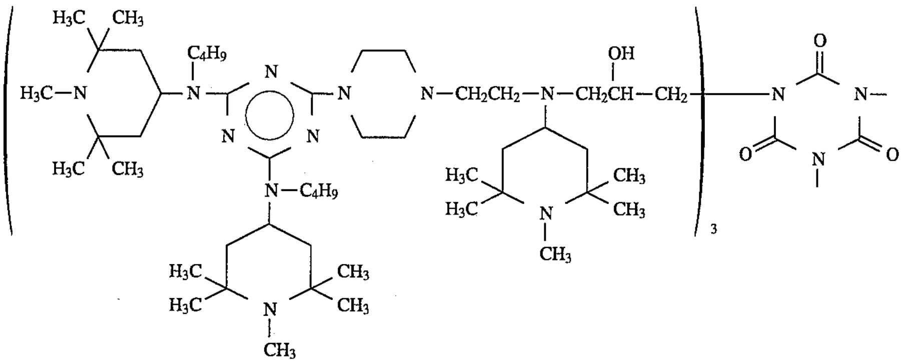

is prepared as described in Example 29, using the compound of Example 25.

The product obtained melts at 159°–162° C.

Analysis for $C_{153}H_{288}N_{36}O_6$

Calculated: C=67.36%; H=10.64%; N=18.48%

Found: C=67.11%; H=10.52%; N=18.41

EXAMPLE 34

The compound of formula

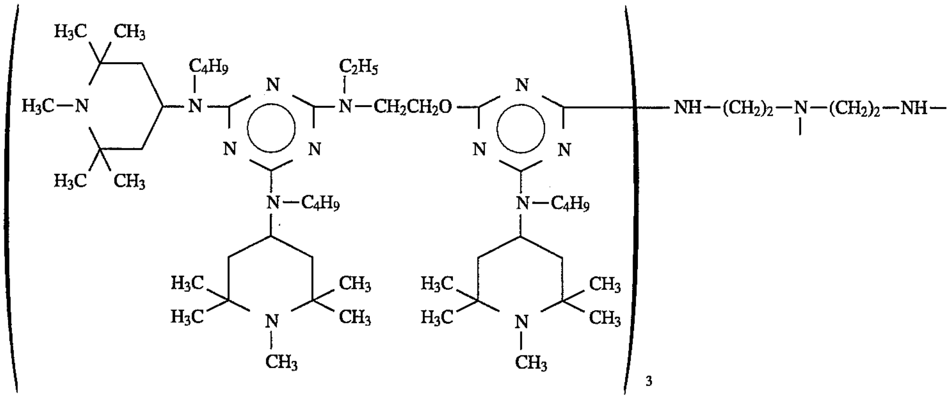

is prepared as described in Example 29, using the compound of Example 27.

The product obtained melts at 151°–154° C.

Analysis for $C_{160}H_{298}N_{42}O_3$

Calculated: C=67.23%; H=10.51%; N=20.58%

Found: C=67.29%; H=10.51%; N=20.47%

EXAMPLE 35

The compound of formula

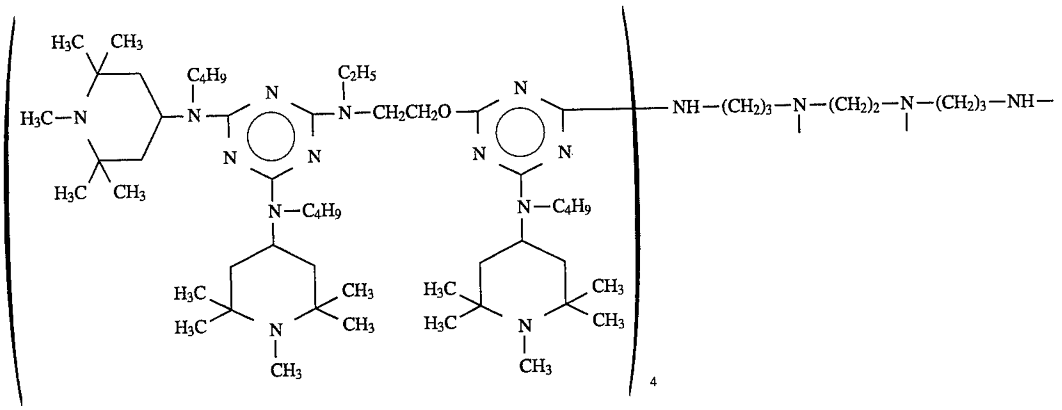

is prepared as described in Example 29, using the compound of Example 28.

The product obtained melts at 141°–145° C.

Analysis for $C_{216}H_{402}N_{56}O_4$

Calculated: C=67.42%; H=10.53%; N=20.38%

Found: C=67.08%; H=10.44%; N=20.36%

EXAMPLE 36

(Light stabilising action in polypropylene fibres)

2.5 g of each of the products indicated in Table 1, 1 g of tris(2,4-di-tert-butylphenyl) phosphite, 0.5 g of calcium monoethyl 3,5-di-tert-butyl-4-hydroxybenzylphosphonate, 1 g of calcium stearate and 2.5 g of titanium dioxide are mixed in a slow mixer with 1000 g of polypropylene powder having a melt index=12 g/10 min (measured at 230° C. and 2.16 kg).

The mixtures are extruded at 200°–230° C. to give polymer granules which are subsequently convened to fibres using a semi-industrial type apparatus (Leonard-Sumirago (VA) Italy) and working under the following conditions:

Extruder temperature: 230°–245° C.

Head temperature: 255°–260° C.

Stretch ratio: 1:3.5

Titre: 11 dtex per filament

The fibres thus prepared are mounted on white card and exposed in a Weather-0-Meter Model 65 WR (ASTM D2565-85) with a black panel temperature of 63° C.

The residual tenacity is measured on the samples, taken after various light exposure times, by means of a constant speed tensometer, after which the exposure time, in hours, required to halve the initial tenacity ($T_{50}$) is calculated. By way of comparison, fibres prepared under the same conditions as indicated above, but without the addition of the stabilisers of the invention, are exposed.

The results obtained are shown in Table 1.

TABLE 1

| Stabiliser | $T_{50}$ (hours) |
|---|---|
| Without stabiliser | 240 |
| Compound of Example 12 | 2900 |
| Compound of Example 14 | 2780 |
| Compound of Example 17 | 2400 |
| Compound of Example 19 | 2150 |
| Compound of Example 20 | 2090 |
| Compound of Example 22 | 2300 |
| Compound of Example 23 | 2370 |
| Compound of Example 24 | 2340 |
| Compound of Example 27 | 2140 |
| Compound of Example 30 | 2180 |

What is claimed is:

1. A compound of formula (Ia)

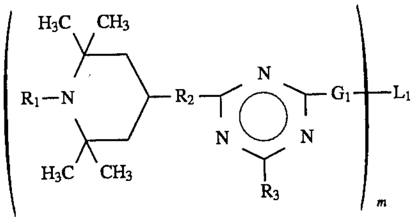

(Ia)

in which $R_1$ is hydrogen, $C_1$–$C_8$alkyl, O., OH, $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or substituted on the phenyl with 1, 2 or 3 $C_1$–$C_4$alkyls, aliphatic $C_1$–$C_8$acyl;

$R_2$ is

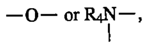

where $R_4$ is hydrogen, $C_1$–$C_{18}$alkyl, $C_5$–$C_{12}$cycloalkyl, which is unsubstituted or substituted with 1, 2 or 3 $C_1$–$C_4$alkyls, $C_7$–$C_7$phenylalkyl which is unsubstituted or substituted on the phenyl with 1, 2 or 3 $C_1$–$C_4$alkyls, tetrahydrofurfuryl, a group of formula (II)

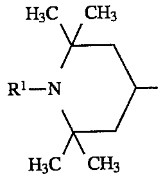

(II)

or $C_2$–$C_4$alkyl which is substituted in the 2, 3 or 4 position with $C_1$–$C_8$alkoxy, with di($C_1$–$C_4$alkyl)amino or with a group of formula (III)

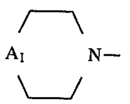

(III)

where $A_1$ is a direct bond, —O—, —$CH_2$—, —$CH_2CH_2$— or

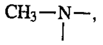

or $R_2$ is also one of the groups of formulae (IVa)-(IVc)

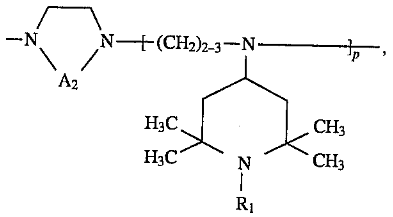

(IVa)

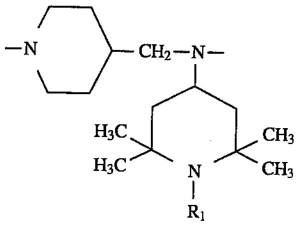

(IVb)

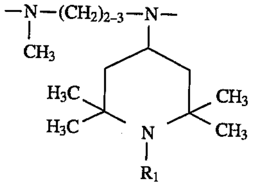

(IVc)

in which $R_1$ is as defined above, $A_2$ is —$CH_2CH_2$—, —CO—, —COCO—, —$CH_2CO$— or —$COCH_2CO$— and p is zero or 1, the nitrogen atom substituted with the piperidyl group being bound to the triazine ring of formula (Ia) or (Ib);

$R_3$ is a group of formula (V)

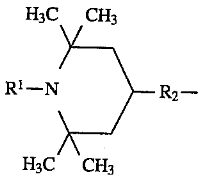

(V)

with $R_1$ and $R_2$ as defined above, or a group of formula (III) or an $R_5O$— or

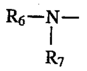

group, where $R_5$, $R_6$ and $R_7$, which are identical or different, are hydrogen, $C_1$–$C_{18}$alkyl, $C_5$–$C_{12}$cycloalkyl which is unsubstituted or substituted with 1, 2 or 3 $C_1$–$C_4$alkyls, $C_8$–$C_{18}$alkenyl, phenyl which is unsubstituted or substituted on the phenyl with 1, 2 or 3 $C_1$–$C_4$alkoxy, $C_7$–$C_9$phenylalkyl which is unsubstituted or substituted in the 2, 3 or 4 position with $C_1$–$C_8$alkoxy or with the di($C_1$–$C_4$alkyl)amino or with a group of formula (III);

$G_1$ is a group of formula (VI)

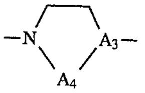

(VI)

in which $A_3$ is a >N—$(R_8—A_5)_q$ group, where $R_8$ is $C_2$–$C_6$alkylene, $A_5$ is —O— or

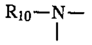

and q is zero or 1, with $R_{10}$ having any one of the meanings given for $R_4$, and $A_4$ is —$CH_2CH_2$— or a

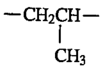

or

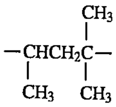

group, the endocyclic nitrogen atom of the formula (VI) being able to be bound to the triazine ring or to the $L_1$ group of formula (Ia);

m is 1, 2, 3 or 4;

if m is 1, $L_1$ is hydrogen, $C_1$–$C_{18}$alkyl, $C_3$–$C_6$alkenyl, $C_7$–$C_9$phenylalkyl which is unsubstituted or substituted on the phenyl with 1, 2 or 3 $C_1$–$C_4$alkyls, aliphatic, cycloaliphatic or aromatic acyl containing not more than 22 carbon atoms or ($C_1$–$C_{18}$alkoxy)carbonyl;

if m is 2, $L_1$ is $C_2$–$C_{12}$alkylene, $C_4$–$C_{12}$alkylene interrupted by 1, 2 or 3 oxygen atoms, phenylenedi($C_1$–$C_4$alkylene), aliphatic, cycloaliphatic or aromatic diacyl containing not more than 20 carbon atoms or one of the groups of formulae (VIIIa)-(VIIId)

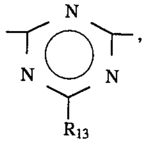

(VIIIa)

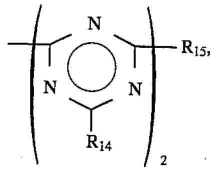

(VIIIb)

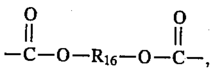

(VIIIc)

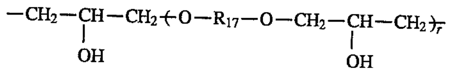

(VIIId)

in which $R_{13}$ has any one of the meanings given for $R_3$ or is a group of formula (IX)

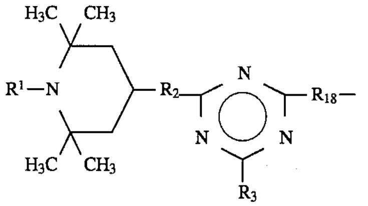

(IX)

where $R_1$, $R_2$ and $R_3$ are as defined above and $R_{18}$ is a group of formula (VI) or a group of formula (VII) as defined above, or $R_{13}$ is also an $R_{18}H$ group, $R_{14}$ has any one of the meanings given for $R_3$ or is a group of formula (IX), $R_{15}$ is a group of formula (Xa) or (Xb)

$$-A_7-R_{19}-A_8-, \quad (Xa)$$

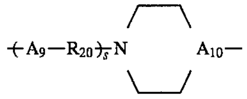

(Xb)

in which $A_7$, $A_8$ and $A_9$, which are identical or different, have any one of the meanings given for $A_5$, $R_{19}$ is $C_2$–$C_{12}$alkylene, $C_4$–$C_{12}$alkylene interrupted by 1,2 or 3 oxygen atoms, $C_5$–$C_7$cycloalkylene, $C_5$–$C_7$cycloalkylenedi($C_1$–$C_4$alkylene), $C_1$–$C_4$ alkylenedi($C_5$–$C_7$cycloalkylene), phenylenedi($C_1$–$C_4$ -alkylene) or is $C_4$–$C_{12}$alkylene interrupted by an

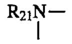

group, where $R_{21}$ has any one of the meanings given for $R_4$ or is an aliphatic, cycloaliphatic or aromatic acyl containing not more than 12 carbon atoms or ($C_1$–$C_{12}$alkoxy)carbonyl, $C_2$–$C_4$alkylidenedi($C_5$–$C_7$ cycloalkylene), phenylene or $C_2$–$C_4$alkylidenediphenylene, each phenylene group being unsubstituted or substituted with 1 or 2 $C_1$–$C_4$alkyls, or $R_{19}$ is a

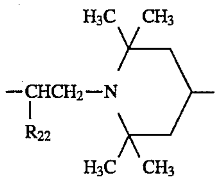

group, with $R_{22}$ being hydrogen or $C_1$–$C_4$alkyl, or a

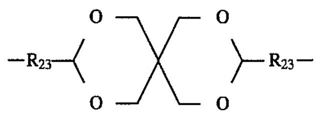

group, $R_{20}$ and $R_{23}$ are $C_2$–$C_6$alkylene, s is zero or 1, $A_{10}$ has any one of the meanings given for $A_3$, $R_{16}$ and $R_{17}$ are $C_2$–$C_{12}$alkylene, $C_4$–$C_{12}$alkylene interrupted by 1, 2 or 3 oxygen atoms, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene), $C_2$–$C_4$alkylenedi($C_5$–$C_7$cycloalkylene), phenylene or $C_2$–$C_4$ alkylidenediphenylene, each phenylene group being unsubstituted or substituted with 1 or 2 $C_1$–$C_4$alkyls, and r is zero or 1;

if m is 3, $L_1$ is aliphatic, cycloaliphatic or aromatic triacyl containing not more than 12 carbon atoms or a group of formula (XIa) or (XIb)

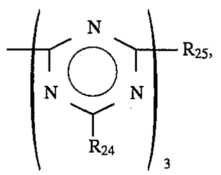

(XIa)

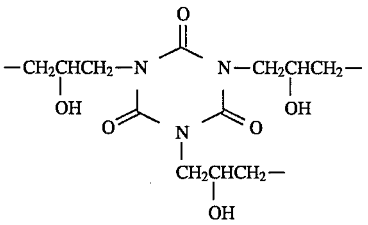

(XIb)

in which $R_{24}$ is as defined above for $R_{14}$ and $R_{25}$ is one of the groups of formulae (XIIA)–(XIId)

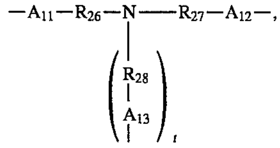

(XIIa)

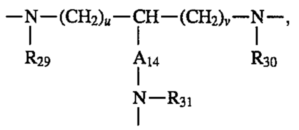

(XIIb)

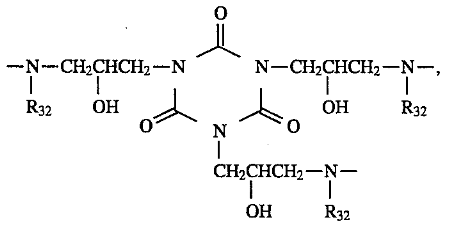

(XIIc)

$$R_{33}(\text{-O-})_3 \quad (XIId)$$

in which $A_{11}$, $A_{12}$ and $A_{13}$, which are identical or different, have any one of the meanings given for $A_5$, $R_{26}$, $R_{27}$ and $R_{28}$, which are identical or different, are $C_2$–$C_6$alkylene, t is zero or 1, $R_{29}$, $R_{30}$, $R_{31}$ and $R_{32}$, which are identical or different, have any one of the meanings given for $R_4$, $A_{14}$ is a direct bond or —$CH_2$—, u and v, which are identical or different, are integers from 2 to 6 and $R_{33}$ is $C_3$–$C_{12}$alkanetriyl; and if m is 4, $L_1$ is aliphatic or aromatic tetraacyl containing not more than 12 carbon atoms, tetrahydrofuran-2,3,4,5-tetracarbonyl or a group of formula (XIII)

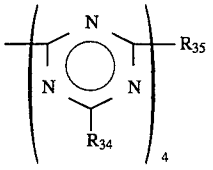

(XIII)

in which $R_{34}$ is as defined above for $R_{14}$ and $R_{35}$ is one of the groups of formulae (XIVa)–(XIVc)

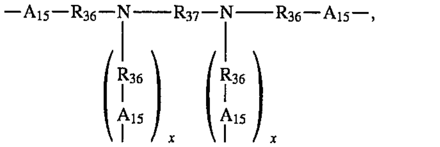

(XIVa)

$R_{38}\text{-}(O\text{-})_4$ (XIVb)

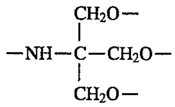

(XIVc)

in which $A_{15}$ has any one of the meanings given for $A_5$, $R_{36}$ and $R_{37}$, which are identical or different, are $C_2$–$C_6$alkylene, x is zero or 1 and $R_{38}$ is $C_4$–$C_{12}$alkanetetrayl.

2. A compound of formula (Ia) according to claim 1, in which $R_2$ is —O— or

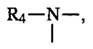

where $R_4$ is hydrogen, $C_1$–$C_{16}$alkyl, $C_5$–$C_8$cycloalkyl which is unsubstituted or substituted with 1, 2 or 3 $C_1$–$C_4$alkyls, benzyl, which is unsubstituted or substituted on the phenyl with 1, 2 or 3 $C_1$–$C_4$alkyls, tetrahydrofurfuryl, a group of formula (II), $C_2$–$C_3$alkyl which is substituted in the 2 or 3 position with $C_1$–$C_4$alkoxy, with di($C_1$–$C_4$alkyl)amino or with a group of formula (III), where $A_1$ is a direct bond, —O—, —$CH_2$— or —$CH_2CH_2$— or $R_2$ is also one of the groups of formulae (IVa)–(IVc), in which $A_2$ is —$CH_2CH_2$—, —CO—, —COCO— or —$COCH_2CO$— and p is zero or 1;

$R_3$ is a group of formula (V) or a group of formula (III) or an $R_5O$— or

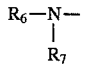

group, where $R_5$, $R_6$ and $R_7$, which are identical or different, are hydrogen, $C_1$–$C_{12}$alkyl, $C_5$–$C_8$cycloalkyl which is unsubstituted or substituted with 1, 2 or 3 $C_1$–$C_4$alkyls, $C_3$–$C_{12}$alkenyl, phenyl which is unsubstituted or substituted with 1, 2 or 3 $C_1$–$C_4$alkyls, or $C_1$–$C_4$alkoxy, benzyl which is unsubstituted or substituted on the phenyl with 1, 2 or 3 $C_1$–$C_4$alkyls, tetrahydrofurfuryl or $C_2$–$C_3$alkyl substituted in the 2 or 3 position with $C_1$–$C_4$alkoxy, with di($C_1$–$C_4$alkyl)amino or with a group of formula (III);

$G_1$ is a group of formula (VI), in which $A_3$ is a >N—($R_8$—$A_5$)$_q$ group, where $R_8$ is $C_2$–$C_4$alkylene, $A_5$ is —O— or

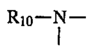

and q is zero or 1, with $R_{10}$ has any one of the meanings given for $R_4$ and $A_4$ is —$CH_2CH_2$— or a

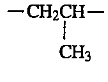 or 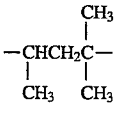

group;

if m is 1, $L_1$ is hydrogen, $C_1$–$C_{16}$alkyl, $C_3$–$C_4$alkenyl, benzyl which is unsubstituted or substituted on the phenyl with 1, 2 or 3 $C_1$–$C_4$alkyls, aliphatic, cycloaliphatic or aromatic acyl containing not more than 18 carbon atoms or ($C_1$–$C_{18}$alkoxy)carbonyl;

if m is 2, $L_1$ is $C_2$–$C_{10}$alkylene, $C_4$–$C_{10}$alkylene interrupted by 1, 2 or 3 oxygen atoms, phenylenedimethylene, aliphatic, cycloaliphatic or aromatic diacyl containing not more than 18 carbon atoms or one of the groups of formulae (VIIIa)–(VIIId), in which $R_{13}$ has any one of the meanings given for $R_3$ or is a group of formula (IX), where $R_{18}$ is a group of formula (VI) or (VII), or $R_{13}$ is also a —$R_{18}$H group, $R_{14}$ has any one of the meanings given for $R_3$ or is a group of formula (IX), $R_{15}$ is a group of formula (Xa) or (Xb), in which $A_7$, $A_8$ and $A_9$, which are identical or different, have any one of the meanings given for $A_5$, $R_{19}$ is $C_2$–$C_{12}$alkylene, $C_4$–$C_{12}$alkylene interrupted by 1,2 or 3 oxygen atoms, $C_5$–$C_7$cycloalkylene, $C_5$–$C_7$cycloalkylenedi($C_1$–$C_4$alkylene), $C_1$–$C_4$ alkylenedi($C_5$–$C_7$cycloalkylene), phenylenedi($C_1$–$C_4$-alkylene) or is $C_4$–$C_{10}$alkylene interrupted by an

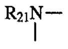

group, where $R_{21}$ has any one of the meanings given for $R_4$ or is an aliphatic, cycloaliphatic or aromatic acyl containing not more than 8 carbon atoms or ($C_1$–$C_8$alkoxycarbonyl), isopropylidenedicyclohexylene, phenylene, isopropylidenediphenylene, a

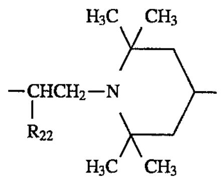

group, with $R_{22}$ being hydrogen or methyl, or a

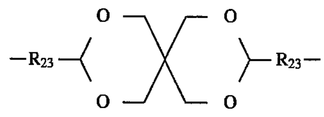

group, $R_{20}$ and $R_{23}$ are $C_2$–$C_4$alkylene, s is zero or 1, $A_{10}$ has any one of the meanings given for $A_3$, $R_{16}$ and $R_{17}$ are $C_2$–$C_{12}$alkylene, $C_4$–$C_{12}$alkylene interrupted by 1, 2 or 3 oxygen atoms, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or are isopropylidenedicyclohexylene, phenylene or isopropylidenedipheylene, and r is zero or 1;

if m is 3, $L_1$ is aliphatic, cycloaliphatic or aromatic triacyl containing not more than 10 carbon atoms or a group of formula (XIa) or (XIb), in which $R_{24}$ is as defined above for $R_{14}$ and $R_{25}$ is one of the groups of formulae (XIIa)–(XIId), in which $A_{11}$, $A_{12}$ and $A_{13}$, which are identical or different, have any one of the meanings given for $A_5$, $R_{26}$, $R_{27}$ and $R_{28}$ which are identical or different, are $C_2$–$C_6$alkylene, t is zero or 1, $R_{29}$, $R_{30}$, $R_{31}$ and $R_{32}$, which are identical or different, have any one of the meanings given for $R_4$, $A_{14}$ is a direct bond or —$CH_2$—, u and v, which are identical or different, are integers from 3 to 6 and $R_{33}$ is $C_3$–$C_{10}$alkanetriyl; and if m is 4, $L_1$ is aliphatic or aromatic tetraacyl containing not more than 10 carbon atoms, tetrahydrofuran-2,3,4,5-tetracarbonyl or a group of formula (XIII), in which $R_{34}$ is as defined above for $R_{14}$ and $R_{35}$ is one of the groups of formulae (XIVa)–(XIVc), in which $A_{15}$ has any one of the meanings given for $A_5$, $R_{36}$ and $R_{37}$, which are identical or different, are $C_2$–$C_4$alkylene, x is zero or 1 and $R_{38}$ is $C_4$–$C_8$alkanetetrayl.

3. A compound of formula (Ia) according to claim 1, in which $R_2$ is —O— or

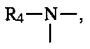

where $R_4$ is hydrogen, $C_1$–$C_{12}$alkyl, cycloalkyl which is unsubstituted or substituted with 1, 2 or 3 $C_1$–$C_4$alkyls, benzyl, tetrahydrofurfuryl, a group of formula (II), $C_2$–$C_3$alkyl which is substituted in the 2 or 3 position with $C_1$–$C_4$alkoxy, with dimethylamino or with 4-morpholinyl, or $R_2$ is also one of the groups of formulae (IVa)–(IVc), in which $A_2$ is $—CH_2CH_2—$, —CO— or —COCO— and p is zero or 1;

$R_3$ is a group of formula (V) or a 4-morpholinyl group or an $R_5O$— or

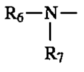

group, where $R_5$, $R_6$ and $R_7$, which are identical or different, are hydrogen, $C_1$–$C_8$alkyl, cyclohexyl which is unsubstituted or substituted with 1, 2 or 3 $C_1$–$C_4$alkyls, $C_3$–$C_{11}$alkenyl, phenyl, benzyl, tetrahydrofurfuryl or $C_2$–$C_3$alkyl which is substituted in the 2 or 3 position with $C_1$–$C_4$alkoxy, with dimethylamino, with diethylamino or with 4-morpholinyl;

$G_1$ is a group of formula (VI), in which $A_3$ is a >N—($R_8$—$A_5)_q$ group, where $R_8$ is $C_2$–$C_4$alkylene, $A_5$ is —O— or

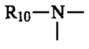

and q is zero or 1, with $R_{10}$ has any one of the meanings given for $R_4$ and $A_4$ is $—CH_2CH_2—$ or a

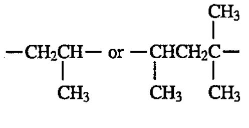

group; and m is 1, 2, 3 or 4;

if m is 1, $L_1$ is hydrogen, $C_1$–$C_{12}$alkyl, allyl, 2-methylallyl, benzyl, aliphatic $C_1$– $C_{12}$acyl or ($C_1$–$C_{12}$alkoxy)carbonyl;

if m is 2, $L_1$ is $C_2$–$C_8$alkylene, $C_4$–$C_8$alkylene interrupted by 1, 2 or 3 oxygen atoms, phenylenedimethylene, aliphatic $C_2$–$C_{16}$diacyl or one of the groups of formula (VIIIa)–(VIIId), in which $R_{18}$ is a group of formula (VI) or (VII), or $R_{13}$ is also a $—R_{18}H$ group, $R_{14}$ has any one of the meanings given for $R_3$ or is a group of formula (IX), $R_{15}$ is a group of formula (Xa) or (Xb), in which $A_7$, $A_8$ and $A_9$, which are identical or different, have any one of the meanings given for $A_5$, $R_{19}$ is $C_2$–$C_{12}$alkylene, $C_4$–$C_{12}$alkylene interrupted by 1,2 or 3 oxygen atoms, $C_5$–$C_7$cycloalkylene, $C_5$–$C_7$cycloalkylenedi($C_1$–$C_4$alkylene), $C_1$–$C_4$ alkylenedi($C_5$–$C_7$cycloalkylene), phenylenedi($C_1$–$C_4$-alkylene) or $R_{19}$ is $C_4$–$C_{10}$alkylene interrupted by a

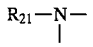

group, where $R_{21}$ has any one of the meanings given for $R_4$ or is an aliphatic $C_1$–$C_4$acyl or ($C_1$–$C_4$alkoxy)carbonyl, isopropylidenedicyclohexylene, isopropylidenediphenylene, a

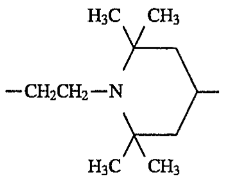

group or a

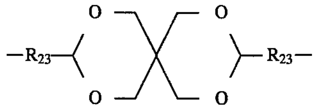

group, $R_{20}$ and $R_{23}$ are $C_2$–$C_4$alkylene, s is zero or 1, $A_{10}$ has any one of the meanings given for $A_3$, $R_{16}$ and $R_{17}$ are $C_2$–$C_{12}$alkylene, $C_4$–$C_{12}$alkylene interrupted by 1, 2 or 3 oxygen atoms, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $R_{16}$ and $R_{17}$ are isopropylidenedicyclohexylene or isopropylidenedipheylene and r is zero or 1;

if m is 3, $L_1$ is aliphatic $C_4$–$C_8$triacyl or a group of formula (XIa) or (XIb), in which $R_{24}$ is as defined above for $R_{14}$ and $R_{25}$ is one of the groups of formulae (XIIa)–(XIId), in which $A_{11}$, $A_{12}$ and $A_{13}$, which are identical or different, have any one of the meanings given for $A_5$, $R_{26}$, $R_{27}$ and $R_{28}$ which are identical or different, are $C_2$–$C_4$alkylene, t is zero or 1, $R_{29}$, $R_{30}$, $R_{31}$ and $R_{32}$, which are identical or different, have any one of the meanings given for $R_4$, $A_{14}$ is a direct bond or $—CH_2—$, u and v, which are identical or different, are integers from 3 to 5 and $R_{33}$ is $C_3$–$C_6$alkanetriyl; and if m is 4, $L_1$ is aliphatic or aromatic tetraacyl or a group of formula (XIII), in which $R_{34}$ is as defined above for $R_{14}$ and $R_{35}$ is one of the groups of formulae (XIVa)–(XIVc), in which $A_{15}$ has any one of the meanings given for $A_5$, $R_{36}$ and $R_{37}$, which are identical or different, are $C_2$–$C_4$alkylene, x is zero or 1 and $R_{38}$ is $C_4$–$C_8$alkanetetrayl.

4. A compound of formula (Ia) according to claim 1, in which $R_2$ is —O— or

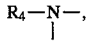

where $R_4$ is hydrogen, $C_1$–$C_8$alkyl, cyclohexyl or a group of formula (II), or $R_2$ is also one of the groups of formulae (IVa)-(IVc), in which $A_2$ is $—CH_2CH_2—$ or —CO— and p is zero or 1;

$R_3$ is a group of formula (V) or a 4-morpholinyl group or an $R_5O—$ or

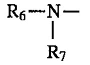

group, where $R_5$ is $C_1$–$C_4$alkyl and $R_6$ and $R_7$, which are identical or different, are hydrogen, $C_1$–$C_4$alkyl or cyclohexyl;

$G_1$ is a group of formula (VI), in which $A_3$ is a >N—($R_8$—$A_5$)$_q$— group, where $R_8$ is $C_2$–$C_3$alkylene, $A_5$ is —O— or

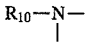

and q is zero or 1, $R_{10}$ has any one of the meanings given for $R_4$ and $A_4$ is $—CH_2CH_2—$ or a

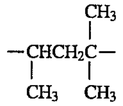

group; and m is 1, 2, 3 or 4;

if m is 1, $L_1$ is hydrogen, $C_1$–$C_8$alkyl, allyl, benzyl, aliphatic $C_1$–$C_8$acyl or ($C_1$–$C_8$alkoxy)carbonyl;

if m is 2, $L_1$ is $C_2$–$C_6$alkylene, $C_4$–$C_6$alkylene interrupted by 1 or 2 oxygen atoms, aliphatic $C_2$–$C_{12}$diacyl or one of the groups of formulae (VIIIa)-(VIIId), in which $R_{13}$ and $R_{14}$ have any one of the meanings given for $R_3$ or are a group of formula (IX), $R_{18}$ is a group of formula (XI) or (VII), $R_{15}$ is a group of formula (Xa) or (Xb), in which $A_7$, $A_8$ and $A_9$, which are identical or different, are an

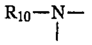

group, $R_{19}$ is $C_2$–$C_{12}$alkylene, $C_4$–$C_{12}$alkylene interrupted by 1,2 or 3 oxygen atoms, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene) or phenylenedi($C_1$–$C_4$-alkylene), $R_{20}$ is $C_2$–$C_3$alkylene, s is zero or 1, $A_{10}$ has any one of the meanings given for $A_3$, $R_{16}$ and $R_{17}$ are $C_2$–$C_6$alkylene, $C_4$–$C_6$alkylene interrupted by 1 or 2 oxygen atoms, isopropylidenedicyclohexylene or isopropylidenediphenylene and r is zero or 1;

if m is 3, $L_1$ is a group of formula (XIa) or (XIb), in which $R_{24}$ is as defined above for $R_{14}$ and $R_{25}$ is a group of formulae (XIIa) or (XIIb), in which t is zero, $A_{11}$ and $A_{12}$ are an

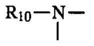

group, $R_{26}$ and $R_{27}$, which are identical or different, are $C_2$–$C_3$alkylene, $R_{29}$, $R_{30}$ and $R_{31}$ have any one of the meanings given for $R_4$, $A_{14}$ is a direct bond or $—CH_2—$ and u and v, which are identical or different, are integers from 3 to 5; and if m is 4, $L_1$ is a group of formula (XIII), in which $R_{34}$ is as defined above for $R_{14}$ and $R_{35}$ is group of formulae (XIVa), in which $A_{15}$ is an

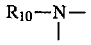

group, $R_{36}$ and $R_{37}$, which are identical or different, are $C_2$–$C_3$alkylene and x is zero.

5. A compound of formula (Ia) according to claim 1, in which $R_1$ is hydrogen or methyl; $R_2$ is —O— or

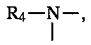

where $R_4$ is hydrogen, $C_1$–$C_4$alkyl or a group of formula (II), or $R_2$ is also a group of formula (IVa), in which $A_2$ is $—CH_2CH_2—$ or —CO— and p is zero or 1; $R_3$ is a group of formula (V); $G_1$ is a

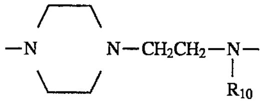

group; and $R_{10}$ has any of the meanings given for $R_4$; and m is 2, 3 or 4; and, if m is 2, $L_1$ is aliphatic $C_2$–$C_{10}$diacyl or one of the groups of formulae (VIIIa)-(VIIId), in which $R_{13}$ and $R_{14}$ are a group of formula (V), a 4-morpholinyl group or a group of formula (IX), where $R_{18}$ is a $G_1$ group, $R_{15}$ is a

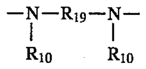

or

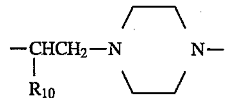

group, $R_{19}$ being $—(CH_2)_{2-6}—$ or $C_8$–$C_{10}$alkylene interrupted by 2 or 3 oxygen atoms, $R_{16}$ is $—(CH_2)_{4-6}$ and r is zero;

if m is 3, $L_1$ is a group of formula (XIa) or (XIb), in which $R_{24}$ is as defined above for $R_{14}$ and $R_{25}$ is a

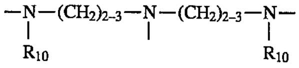

group; and if m is 4, $L_1$ is a group of formula (XIII), in which $R_{34}$ is as defined above for $R_{14}$ and $R_{35}$ is a

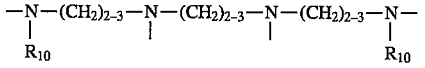

group.

6. A compound of formula (Ia) according to claim 1, in which $R_1$ is hydrogen, $C_1$–$C_4$alkyl, OH, $C_6$–$C_{12}$alkoxy, $C_5$–$C_8$cycloalkoxy, allyl, benzyl or acetyl.

* * * * *